United States Patent

Overes

(10) Patent No.: US 9,532,817 B2
(45) Date of Patent: Jan. 3, 2017

(54) INTRAMEDULLARY NAIL HAVING SELF-RETAINING COMPRESSION SLOT

(71) Applicant: DePuy Synthes Products, Inc., Raynham, MA (US)

(72) Inventor: Tom Overes, Langendorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 47 days.

(21) Appl. No.: 14/323,068

(22) Filed: Jul. 3, 2014

(65) Prior Publication Data

US 2014/0316410 A1 Oct. 23, 2014

Related U.S. Application Data

(63) Continuation of application No. 13/372,583, filed on Feb. 14, 2012, now Pat. No. 8,771,271.

(Continued)

(51) Int. Cl.
*A61B 17/56* (2006.01)
*A61B 17/58* (2006.01)
(Continued)

(52) U.S. Cl.
CPC ....... *A61B 17/7225* (2013.01); *A61B 17/1725* (2013.01); *A61B 17/7241* (2013.01); *A61B 2017/1778* (2013.01)

(58) Field of Classification Search
CPC . A61B 17/164; A61B 17/921; A61B 17/1725; A61B 17/72; A61B 17/7216; A61B 17/7225; A61B 17/725; A61B 17/7233; A61B 17/7241; A61B 17/7291; A61B 17/744

(Continued)

(56) References Cited

U.S. PATENT DOCUMENTS 4,805,607 A * 2/1989 Engelhardt et al. ............ 606/67
4,875,475 A * 10/1989 Comte ............... A61B 17/7225
606/64

(Continued)

FOREIGN PATENT DOCUMENTS

DE 29923467 10/2000
DE 20 2004014288 11/2004
(Continued)

OTHER PUBLICATIONS

U.S. Appl. No. 61/442,397, filed Feb. 14, 2011, Overes.
(Continued)

*Primary Examiner* — Eduardo C Robert
*Assistant Examiner* — Michelle C Eckman
(74) *Attorney, Agent, or Firm* — Wayne C. Jaeschke, Jr.

(57) ABSTRACT

An intramedullary nail has a scalloped compression slot so as to define a plurality of pockets and intersections between the pockets that are narrower than the pockets. Accordingly, a compression member can be inserted into a bone segment of a fractured bone and into the slot. The compression member can be wider than the intersections. A compression actuator can apply a force against the compression member that causes the compression member to translate across the intersections from pocket-to-pocket until the fracture has been approximated. Because the compression member is wider than the intersections, the compression slot retains the compression member and prevents distraction of the fracture.

3 Claims, 23 Drawing Sheets

Related U.S. Application Data

(60) Provisional application No. 61/442,397, filed on Feb. 14, 2011.

(51) Int. Cl.
*A61F 2/30* (2006.01)
*A61B 17/72* (2006.01)
*A61B 17/17* (2006.01)

(58) Field of Classification Search
USPC .................. 606/60, 62–68, 246, 280–282
See application file for complete search history.

(56) References Cited

U.S. PATENT DOCUMENTS

| | | | |
|---|---|---|---|
| 5,324,290 A | 6/1994 | Zdeblick et al. | |
| 5,743,908 A * | 4/1998 | Kim | 606/64 |
| 6,106,528 A * | 8/2000 | Durham et al. | 606/64 |
| 6,120,504 A * | 9/2000 | Brumback et al. | 606/62 |
| 6,168,595 B1 * | 1/2001 | Durham et al. | 606/64 |
| 6,228,086 B1 * | 5/2001 | Wahl et al. | 606/67 |
| 6,406,478 B1 | 6/2002 | Kuo | |
| 6,562,042 B2 * | 5/2003 | Nelson | 606/62 |
| 6,569,165 B2 * | 5/2003 | Wahl et al. | 606/67 |
| 6,579,294 B2 * | 6/2003 | Robioneck | 606/64 |
| 6,932,819 B2 * | 8/2005 | Wahl et al. | 606/67 |
| 7,335,203 B2 | 2/2008 | Winslow et al. | |
| 7,410,488 B2 * | 8/2008 | Janna et al. | 606/62 |
| 7,722,653 B2 * | 5/2010 | Young et al. | 606/280 |
| 7,763,021 B2 * | 7/2010 | Cole et al. | 606/64 |
| 7,776,038 B2 * | 8/2010 | Prien | 606/67 |
| 7,905,883 B2 | 3/2011 | Bruecker et al. | |
| 7,914,561 B2 * | 3/2011 | Konieczynski et al. | 606/280 |
| 8,157,802 B2 * | 4/2012 | Elghazaly et al. | 606/64 |
| 8,252,032 B2 * | 8/2012 | White et al. | 606/280 |
| 8,328,807 B2 * | 12/2012 | Brigido | 606/64 |
| 8,771,271 B2 | 7/2014 | Overes | |
| 2001/0012939 A1 * | 8/2001 | Wahl et al. | 606/67 |
| 2002/0156473 A1 * | 10/2002 | Bramlet et al. | 606/62 |
| 2003/0114855 A1 * | 6/2003 | Wahl et al. | 606/67 |
| 2004/0127900 A1 | 7/2004 | Konieczynski et al. | |
| 2005/0107791 A1 * | 5/2005 | Manderson | 606/62 |
| 2005/0251138 A1 | 11/2005 | Boris et al. | |
| 2005/0273103 A1 * | 12/2005 | Wahl et al. | 606/62 |
| 2006/0064096 A1 * | 3/2006 | Prien | 606/64 |
| 2006/0095039 A1 * | 5/2006 | Mutchler | 606/64 |
| 2006/0200141 A1 * | 9/2006 | Janna et al. | 606/62 |
| 2007/0100343 A1 * | 5/2007 | Cole et al. | 606/67 |
| 2007/0213725 A1 * | 9/2007 | Hack | 606/62 |
| 2008/0021471 A1 | 1/2008 | Winslow et al. | |
| 2008/0082102 A1 * | 4/2008 | Bruecker et al. | 606/69 |
| 2008/0140129 A1 * | 6/2008 | Dalton | 606/280 |
| 2008/0221577 A1 * | 9/2008 | Elghazaly | 606/64 |
| 2008/0262496 A1 * | 10/2008 | Schlienger et al. | 606/62 |
| 2008/0294164 A1 * | 11/2008 | Frank et al. | 606/64 |
| 2009/0048598 A1 * | 2/2009 | Ritchey | A61B 17/1725 606/57 |
| 2009/0048600 A1 * | 2/2009 | Matityahu et al. | 606/62 |
| 2009/0149861 A1 * | 6/2009 | Brodsky et al. | 606/96 |
| 2009/0171399 A1 * | 7/2009 | White et al. | 606/286 |
| 2009/0254126 A1 * | 10/2009 | Orbay et al. | 606/282 |
| 2009/0292318 A1 * | 11/2009 | White et al. | 606/281 |
| 2010/0094293 A1 * | 4/2010 | McClellan et al. | 606/64 |
| 2010/0268229 A1 * | 10/2010 | Siravo et al. | 606/64 |
| 2011/0054473 A1 * | 3/2011 | Brigido | 606/62 |
| 2011/0118742 A1 * | 5/2011 | Hulliger et al. | 606/70 |
| 2011/0144700 A1 * | 6/2011 | Konieczynski et al. | 606/289 |
| 2011/0282395 A1 * | 11/2011 | Beyar et al. | 606/301 |
| 2012/0109127 A1 * | 5/2012 | Overes | 606/64 |
| 2012/0130370 A1 * | 5/2012 | Kinmon | 606/62 |
| 2012/0136356 A1 * | 5/2012 | Doherty et al. | 606/64 |
| 2012/0157997 A1 * | 6/2012 | Sohngen | 606/64 |
| 2012/0191092 A1 * | 7/2012 | Buettler et al. | 606/64 |
| 2012/0191138 A1 * | 7/2012 | Kiester | 606/281 |
| 2012/0197255 A1 * | 8/2012 | Elghazaly | 606/64 |
| 2012/0197303 A1 * | 8/2012 | King et al. | 606/282 |
| 2012/0209268 A1 * | 8/2012 | Overes | 606/62 |
| 2012/0330313 A1 * | 12/2012 | Grady et al. | 606/64 |

FOREIGN PATENT DOCUMENTS

| | | |
|---|---|---|
| EP | 1557131 | 7/2005 |
| WO | WO 96/35387 | 11/1996 |
| WO | WO 2012/112495 | 8/2012 |

OTHER PUBLICATIONS

International Patent Application No. PCT/US2012/024978: International Search Report and Written Opinion dated Apr. 25, 2012, 13 pages.

* cited by examiner

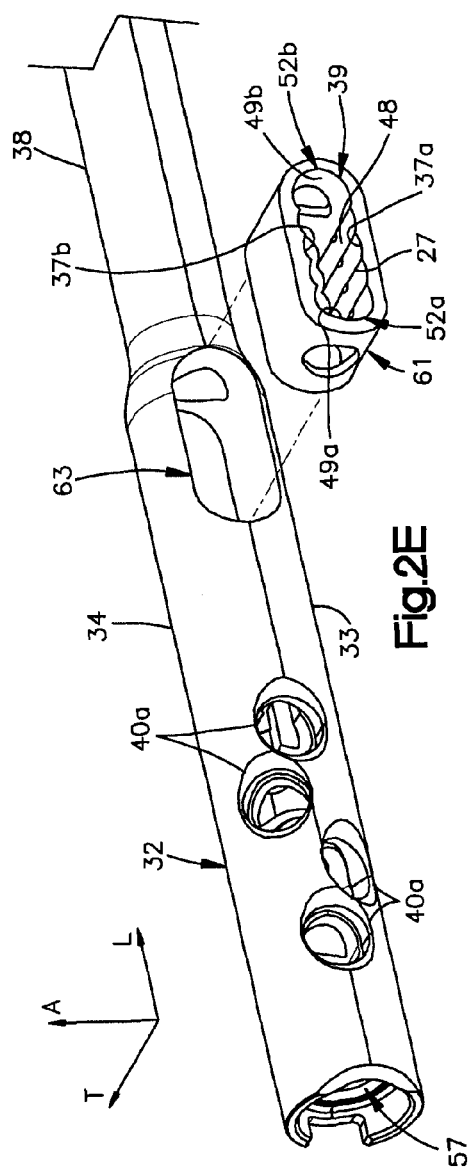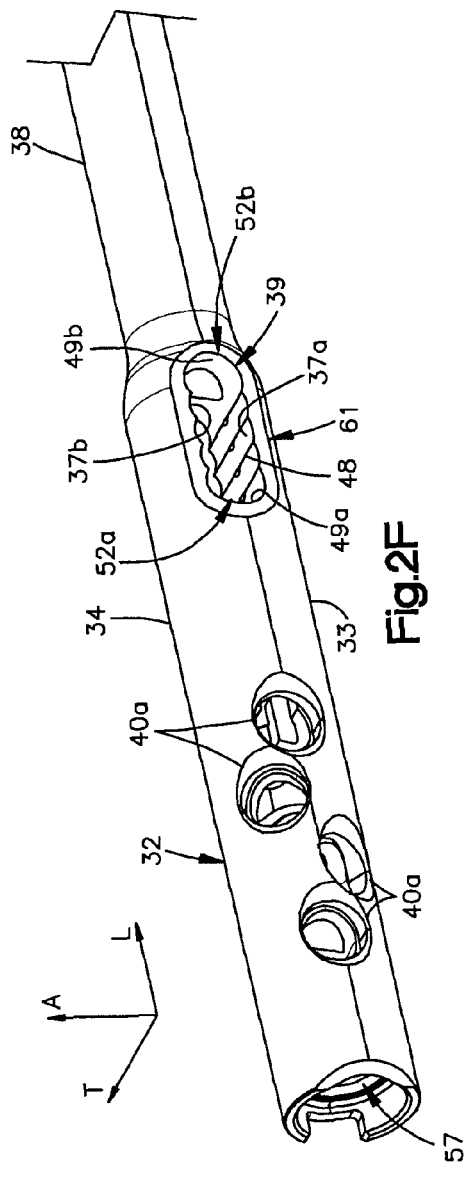

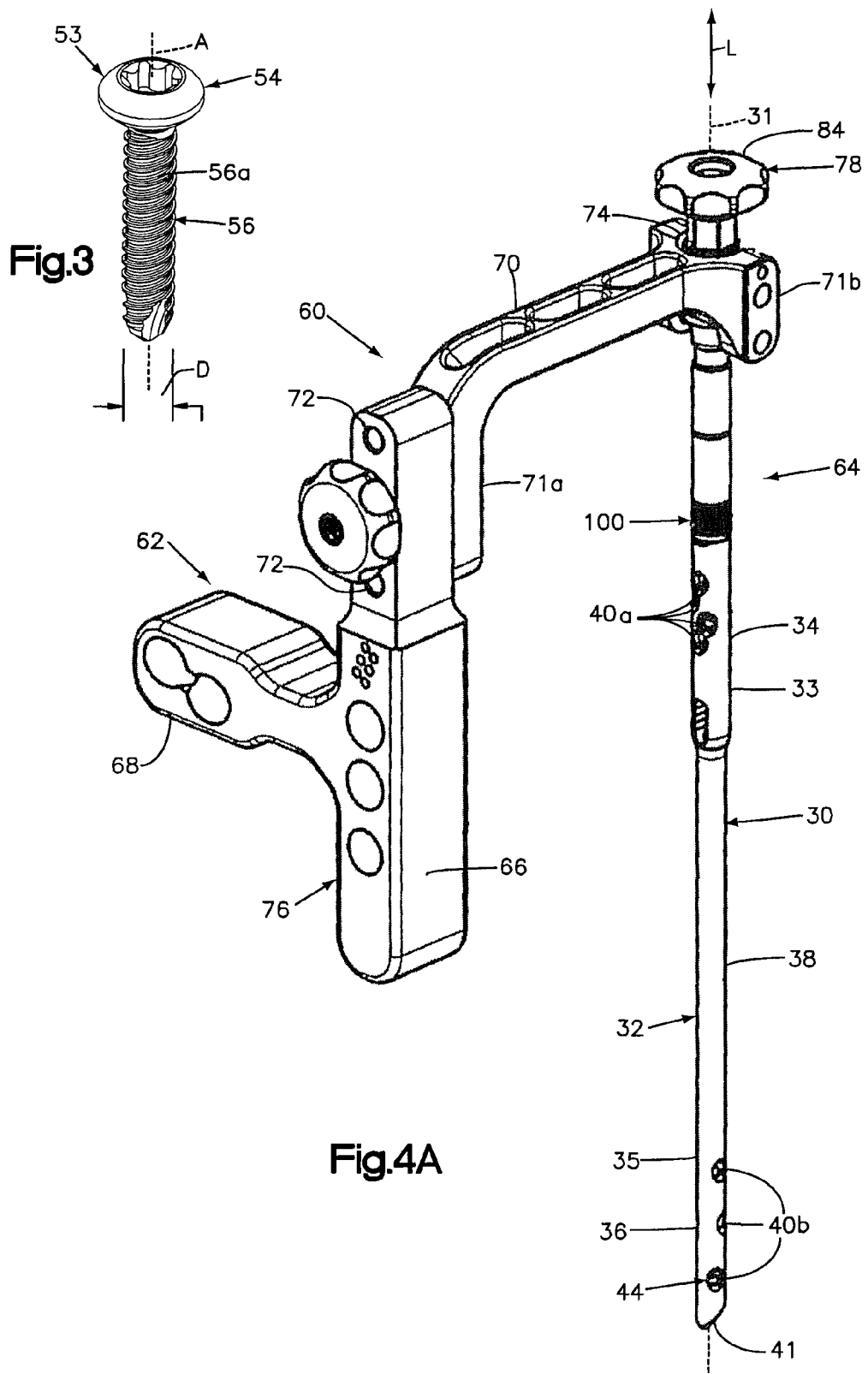

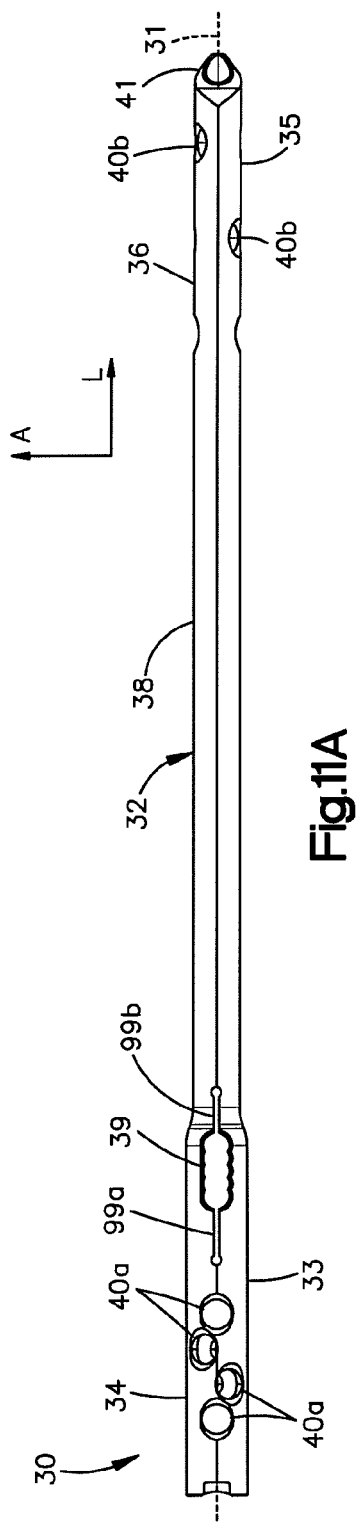
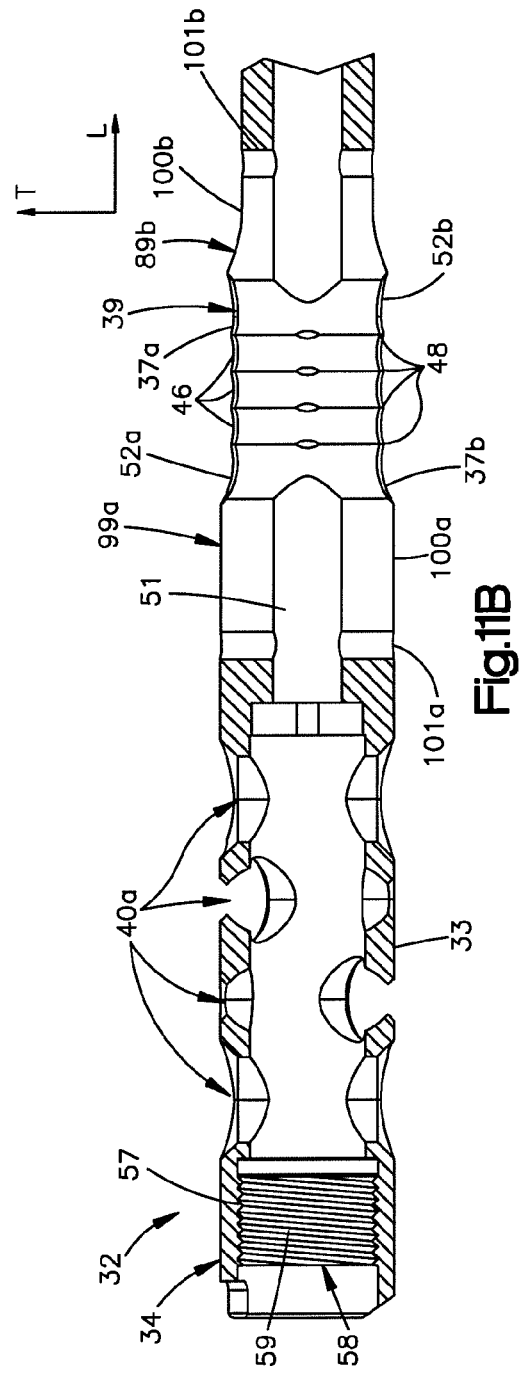
Fig.11A
Fig.11B

INTRAMEDULLARY NAIL HAVING SELF-RETAINING COMPRESSION SLOT

CROSS-REFERENCE TO RELATED APPLICATIONS

This is a continuation application of U.S. patent application Ser. No. 13/372,583 filed Feb. 14, 2012 which in turn claims the benefit of U.S. patent application Ser. No. 61/442,397 filed on Feb. 14, 2011, the disclosure of each of which is hereby incorporated by reference as if set forth in its entirety herein.

BACKGROUND

Conventional intramedullary nails are configured to be inserted into the medullary canal of a long bone that has been fractured so as to define a proximal bone segment and a distal bone segment that is separated from the proximal bone segment by a bone gap. Conventional intramedullary nails are elongate along a substantially central longitudinal axis, and include a plurality of bone anchor holes that extend through the nail along respective axes that are angularly offset, for instance perpendicular, with respect to the longitudinal axis of the intramedullary nail, and configured to receive bone anchors. For instance, the bone anchor holes can be substantially smooth and configured to receive screws, or can be threaded so as to mate with screws to increase axial stability. The bone anchor holes can be divided into a first plurality of proximal bone anchor holes that extend through the proximal portion of the intramedullary nail and a second plurality of distal bone anchor holes that extend through the distal portion of the intramedullary nail. Thus, the intramedullary nail can be inserted into the medullary canal of the fractured long bone such that the proximal bone anchor holes are aligned with the proximal bone segment and the distal bone anchor holes are aligned with the distal bone segment on opposite sides of the bone gap. The bone screws can be driven into the bone segments and the corresponding bone anchor holes so as to fasten the intramedullary nail to the fractured long bone and stabilize the proximal and distal bone segments relative to each other, thereby promoting healing.

Certain conventional intramedullary nails include compression features that cause the proximal and distal bone segments to compress toward each other, thereby approximating the bone gap. For instance, screws can be inserted into the distal bone segment and the distal bone anchor holes of the intramedullary nail so as to fix the distal bone segment to the distal intramedullary nail, and the compression feature can be actuated to cause the proximal bone segment to translate relative to the intramedullary nail toward the distal bone segment. However, certain conventional compression features, while facilitating the approximation of the bone gap, are not self-retaining. Accordingly, compression is maintained manually while fixing the distal bone segment to the distal portion of the intramedullary nail. Other compression features are self-retaining so as to maintain approximation of the bone gap while the distal bone segment is fixed to the distal portion of the intramedullary nail. However, conventional self-retaining compression features typically add movable components in the intramedullary nail and are time consuming and complex to use.

SUMMARY

In accordance with one aspect, an intramedullary nail includes a nail body that defines a first portion that is positioned to attach to a first bone segment and a second portion that is spaced from the first portion substantially along a longitudinal direction and positioned to attach to a second bone segment that is separated from the first bone segment by a bone gap. The nail body defines a scalloped slot that extends into the first portion of the nail body, the slot defining at least a pair of longitudinally spaced pockets and an intersection between the pockets. The compression slot defines a first width substantially perpendicular to the longitudinal direction between opposed ones of the intersections, and the compression defines a second width between opposed ones of the pockets along a direction substantially parallel to the first width, such that the second width is greater than the first width.

BRIEF DESCRIPTION OF THE DRAWINGS

The foregoing summary, as well as the following detailed description of the preferred embodiments of the application, will be better understood when read in conjunction with the appended drawings. For the purposes of illustrating the present disclosure, there is shown in the drawings preferred embodiments. It should be understood, however, that the application is not limited to the specific embodiments and methods disclosed, and reference is made to the claims for that purpose. In the drawings:

FIG. 2E is a perspective view of the proximal portion of the nail body illustrated in FIG. 2A, but constructed in accordance with an alternative embodiment, showing the nail body including an insert that is attachable to the proximal portion;

FIG. 2F is a perspective view of the proximal portion of the nail body illustrated in FIG. 2A, showing the insert attached to the proximal portion;

FIG. 3 is a side elevation view of a compression member configured to extend into the compression slot of the intramedullary nail illustrated in FIG. 2A;

FIG. 4A is a perspective view of a fixation system including an implantation assembly that includes a support frame and a brace member, and a bone fixation assembly that includes the intramedullary nail illustrated in FIG. 2A, showing the brace member coupled to the intramedullary nail;

FIG. 11A is a side elevation view of an intramedullary nail similar to the intramedullary nail illustrated in FIG. 2A, but including a relief slot in accordance with another embodiment;

FIG. 11B is a sectional side elevation view of a proximal portion of the intramedullary nail illustrated in FIG. 11A;

DETAILED DESCRIPTION

Figure 1:
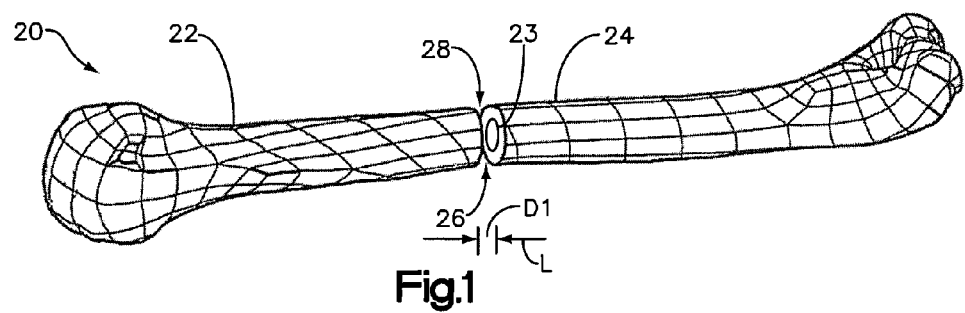
FIG. 1 is a perspective view of a fractured long bone that defines a proximal bone segment and a distal bone segment separated from the proximal bone segment by a bone gap.

Referring to FIG. 1, a long bone 20 that is elongate substantially along a longitudinal direction is fractured so as to define a first or proximal bone segment 22 and a second distal bone segment 24 that is separated from the proximal bone segment 22 by a longitudinal bone gap 26 at a fracture location 28. It should be appreciated that the fractured long bone 20 can define a single fracture location 28 as illustrated, or can define multiple fracture locations that separate additional bone segments from each other at respective bone gaps. While the long bone 20 is a humerus in accordance with the illustrated embodiment, the long bone 20 can be any long bone in the body that defines a medullary canal 23 suitable to receive an intramedullary nail so as to fix the proximal bone segment 22 to the distal bone segment 24. However, because the bone gap 26 defines a bone gap distance D1 that extends along a longitudinal direction L and is greater than a desired distance suitable for reliable fixation of the proximal bone segment 22 to the distal bone segment 24, it is desirable for the intramedullary nail to include a compression feature that is configured to approximate the bone gap 26 to a distance that allows for reliable fixation of the bone segments 22 and 24 across the bone gap 26 during healing.

Figure 2A:
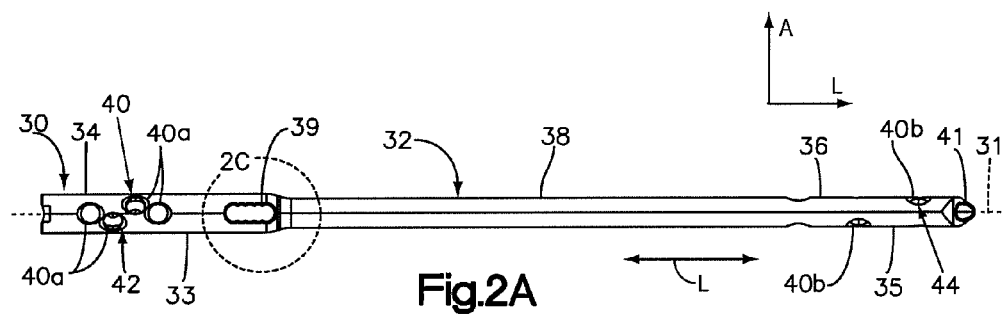
FIG. 2A is a side elevation view of an intramedullary nail having a proximal portion, a distal portion, a plurality of proximal bone anchor holes extending through the proximal portion, a plurality of distal bone anchor holes extending through the distal portion, and a self-retaining compression slot extending along the proximal bone segment.
Figure 2B:
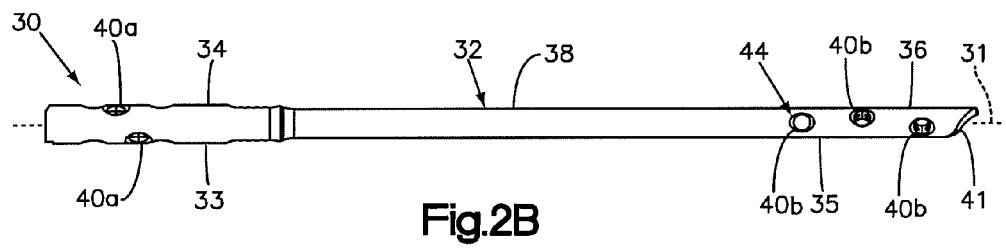
FIG. 2B is another side elevation view of the intramedullary nail illustrated in FIG. 2A.
Figure 2C:
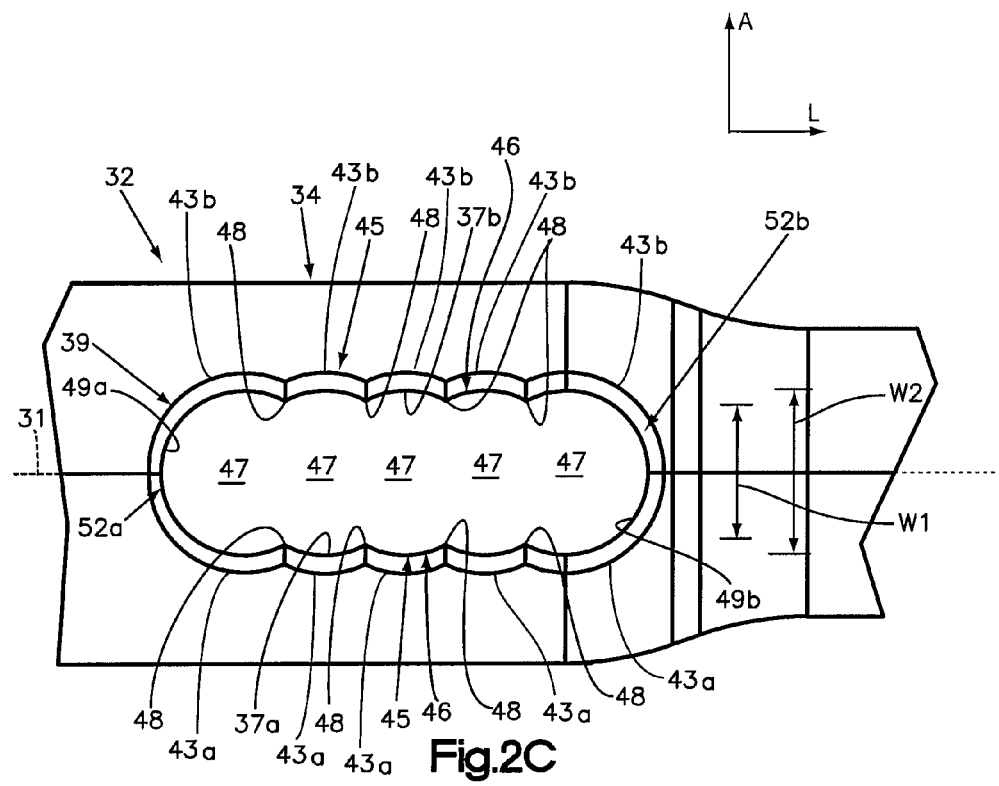
FIG. 2C is an enlarged side elevation view of the compression slot illustrated in FIG. 2A.
Figure 2D:
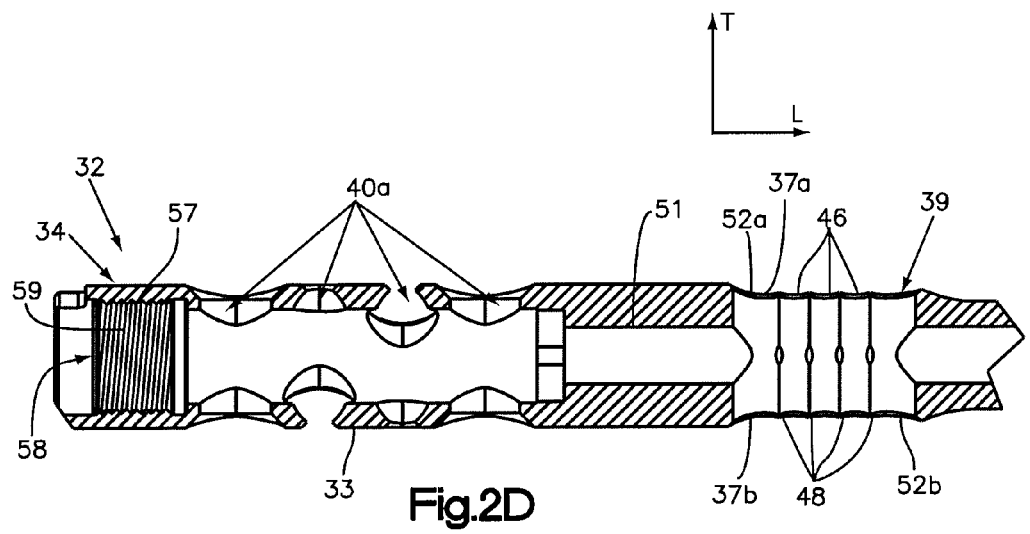
FIG. 2D is a sectional side elevation view of a proximal portion of the intramedullary nail illustrated in FIG. 2A.

Referring now to FIGS. 1-2D, an intramedullary nail 30 constructed in accordance with one embodiment includes a nail body 32 that is elongate substantially along a longitudinal axis 31 that extends substantially along the longitudinal direction L. For instance, it should be appreciated that the nail body 32 extend straight along the longitudinal direction L or can be slightly curved along the longitudinal direction. The intramedullary nail 30 can be inserted into the medullary canal 23 of the long bone such that the longitudinal axis 31 extends along the medullary canal 23. In accordance with one embodiment, the longitudinal axis 31 can define a central axis of the nail body 32. The nail body 32 can define any suitable shape as desired, and is substantially cylindrical in cross section along a plane that is substantially perpendicular to the longitudinal axis 31 in accordance with the illustrated embodiment. The nail body 32 defines a proximal portion 34 and an opposed distal portion 36 that is spaced distally with respect to the proximal portion 34 along the longitudinal axis 31, and an intermediate portion 38 disposed between the proximal portion 34 and the distal portion 36.

The nail body 32 further defines a first portion 33 that is positioned to attach to the first or proximal bone segment 22, and an opposed second portion 35 that is spaced from the first portion 33 along the longitudinal direction and positioned to attach to the second or distal bone segment 24, such that the intermediate portion 38 extends between the first and second portions 33 and 35. In accordance with the illustrated embodiment, the first portion 33 defines the proximal portion 34 of the nail body 32 and the second portion 35 is defines the distal portion 36 of the nail body 32. Alternatively, as will be described in more detail below, the first portion 33 can define the distal portion 36 of the nail body 32 and the second portion 35 can define the proximal portion 34 of the nail body 32.

The intramedullary nail 30 further defines a plurality of bone anchor holes 40 that extend into, and can further extend through, the nail body 32, for instance along a direction that is angularly offset, such as substantially perpendicular, with respect to the longitudinal axis 31. The bone anchor holes 40 can be sized to receive complementary bone anchors that are configured to secure the intramedullary nail 30 to the long bone 20. For instance, the bone anchor holes 40 can receive any suitable respective bone anchors such as nails or screws that fasten the intramedullary nail 30 to the long bone 20. At least a portion of the bone anchor holes 40 can be threaded so as to threadedly mate with complementary threaded portions of certain select ones up to all of the bone screws. Thus, the bone anchor holes 40 can be threaded, unthreaded, or threaded along a portion of their length along the transverse direction T. The bone anchor holes 40 can include at least one such as a plurality of first bone anchor holes 40a disposed at the first portion 33 of the nail body 32, and at least one such as a plurality of second bone anchor holes 40b disposed at the second portion 35 of the nail body 32.

The intramedullary nail 30 is configured to be initially inserted into the medullary canal 23 of the long bone 20 such that the first portion 33 is disposed in the medullary canal 23 of the proximal bone segment 22, the second portion 35 is disposed in the medullary canal 23 of the distal bone segment 24, and the intermediate portion 38 extends across the bone gap 26, when the first portion 33 defines the proximal portion 34 of the nail body 32 and the second portion 35 defines the distal portion 36 of the nail body 32. Alternatively, the intramedullary nail 30 is configured to be initially inserted into the medullary canal 23 of the long bone 20 such that the first portion 33 is disposed in the medullary canal 23 of the distal bone segment 24, the second portion 35 is disposed in the medullary canal 23 of the proximal bone segment 22, and the intermediate portion 38 extends across the bone gap 26, when the first portion 33 defines the distal portion 36 of the nail body 32 and the second portion 35 defines the proximal portion 34 of the nail body 32. Thus, the intermediate portion 38 can be sized so as to define a length in the longitudinal direction L that is greater than the bone gap distance D1. Of course, it should be appreciated that the proximal portion 34 or the distal portion 36 can extend across the bone gap 26 so long as the bone gap 26 is disposed longitudinally between at least one of the first bone anchor holes 40a and at least one of the second bone anchor holes 40b.

The nail body 32 defines first and second internal surfaces 37a and 37b that are spaced along a lateral direction A that extends substantially perpendicular to the longitudinal direction L. The first and second internal surfaces 37a and 37b can be spaced substantially equidistantly from the longitudinal axis 31, or can be spaced such that one of the first and second internal surfaces 37a and 37b is spaced closer to or further from the longitudinal axis 31 than the other of the first and second internal surfaces 37a and 37b. The first and second internal surfaces 37a and 37b define a compression slot 39 that extends into, and can further extend through, the first portion 33 of the nail body 32 along a transverse direction T that is substantially perpendicular to the longitudinal direction L and the lateral direction A.

The compression slot 39 can be elongate along the longitudinal direction L. The first portion 33 of the nail body 32 can define a cannulation 51 that extends at least from a corresponding longitudinally outer terminal end of the first portion 33 of the nail body 32 through the compression slot 39. It should be appreciated that the second portion 35 can also define a second compression slot constructed as described herein with respect to the compression slot 39 so as to provide positional flexibility when the intramedullary nail 30 is inserted into the medullary canal of the fractured long bone 20. Thus, description herein of the first portion 33 as including the compression slot 39 can apply equally to the second portion 35 when the second portion 35 defines the compression slot 39 or a second compression slot. For instance, the nail body 32 can define a cannulation that extends from a corresponding longitudinally outer terminal end of the second portion 35 of the nail body 32 through the compression slot disposed in the second portion 35.

As is described in more detail below, the compression slot 39 is a self-retaining compression slot that is configured to at least temporarily retain a compression member 53 (see FIG. 3) that extends into the compression slot 39 in a desired longitudinal position that reduces the bone gap 26. In accordance with the illustrated embodiment, the compression slot 39 extends into the proximal portion 34 of the nail body 32, though it should be appreciated that the compression slot 39 can alternatively extend into the distal portion 36 of the nail body 32. The first portion 33 of the nail body 32 can define a cross-sectional distance, such as a diameter, that is greater than that of one or both of the second portion 35 and the intermediate portion 38 of the nail body 32. Otherwise stated, the portion of the intramedullary nail 30 that defines the compression slot 39, such as the proximal portion 34, can define a cross-sectional distance, such as a diameter, that is greater than that of one or both of the other portions of the intramedullary nail 30.

As described above, the intramedullary nail 30 defines a plurality of bone anchor holes 40 that extend into, and can further extend through, the nail body 32. The plurality of bone anchor holes 40 can include at least one first bone anchor hole 40a such as a plurality of first bone anchor holes 40a that are disposed adjacent the compression slot 39 in first portion 33 of the intramedullary nail 30 that defines the compression slot 39, and at least one second bone anchor hole 40b such as a plurality of second bone anchor holes 40b that are disposed in the second portion 35 of the intramedullary nail 30. In accordance with the illustrated embodiment, the plurality of first bone anchor holes 40a are configured as proximal bone anchor holes that extend into the proximal portion 34 of the intramedullary nail 30, and the plurality of second bone anchor holes 40b are configured as distal bone anchor holes that extend into the distal portion 36 of the intramedullary nail 30. One or more up to all of the plurality of first bone anchor holes 40a can be disposed longitudinally outward with respect to the compression slot 39, such that the compression slot 39 is disposed longitudinally between the first bone anchor holes 40a and the second end 35. Alternatively or additionally, one or more up to all of the plurality of first bone anchor holes 40a can alternatively or additionally be disposed longitudinally inward with respect to the compression slot 39, such that the first bone anchor holes 40a are disposed longitudinally between the compression slot 39 and the second end 35. For instance, in accordance with the illustrated embodiment, the plurality of first bone anchor holes 40a can include bone anchor holes 40a that are disposed proximal of the compression slot 39, though the plurality of first 42 bone anchor holes 40a can alternatively or additionally include bone anchor holes 40a that are disposed distal of the compression slot 39. If the compression slot 39 is disposed in the distal portion 36 of the nail body 32, the plurality of first bone anchor holes 40a can include bone anchor holes 40a that are disposed distal of the compression slot 39, though the plurality of first bone anchor holes 40a can alternatively or additionally include bone anchor holes 40a that are disposed proximal of the compression slot 39.

At least some up to all of the first and second pluralities 42 and 44 of bone anchor holes 40 can be longitudinally spaced from each other, and can alternatively or additionally be radially offset with respect to each other. Furthermore, the bone anchor holes 40 can extend along respective central axes that are angularly offset with respect to the longitudinal axis 31. In accordance with the illustrated embodiment, at least one up to all of the bone anchor holes 40 can extend along respective central axes that are substantially perpendicular to the longitudinal axis 31. The central axes of one or more up to all of the bone anchor holes 40 can be substantially parallel with respect to each other, and alternatively or additionally, the central axes of one or more up to all of the bone anchor holes 40 can be substantially angularly offset with respect to each other.

Referring now to FIGS. 2C-D in particular, the internal surfaces 37a and 37b can be elongate substantially in the longitudinal direction L. The internal surfaces 37a and 37b can be spaced from each other along the lateral direction A. At least one or both of the internal surfaces 37a and 37b can be scalloped along the longitudinal direction L such that the compression slot 39 can also be referred to as a scalloped compression slot. For instance, at least one or both of the internal surfaces 37a and 37b can define a series of first and second regions 43a and 43b, respectively, that are concave with respect to the compression slot 39 so as to define a respective plurality of pockets 45 in the compression slot 39. In accordance with the illustrated embodiment, each of the internal surfaces 37a and 37b defines four pockets 45, though it should be appreciated that the internal surfaces 37a and 37b can define any number of pockets 45 including two or more. In accordance with one embodiment, at least one of the internal surfaces 37a and 37b can define at least three pockets 45 that are spaced along the longitudinal direction L so as to provide for fine increments of compression. The first regions 43a are spaced from each other along the longitudinal direction L and the second regions 43b are spaced from each other along the longitudinal direction L. The first regions 43a are spaced from the second regions 43b along the lateral direction A.

The first and second internal surfaces 37a and 37b can define respective necked portions that can be defined by intersections 48 connected between adjacent ones of the first regions 43a, and necked portions that can be defined by respective intersections 48 that are connected between adjacent ones of the second regions 43b. Opposite ones of the first regions 43a and second regions 43b along the lateral direction A can be aligned such that straight lines extending perpendicular to the longitudinal axis 31, for instance along the lateral direction A, intersect, for instance bisect, pairs of opposed pockets 45, and straight lines extending perpendicular to the longitudinal axis 31, for instance along the lateral direction A intersect, for instance bisect, opposed intersections 48 of the opposed internal surfaces 37a and 37b. Thus, it can be said that the compression slot 39 can define a plurality of holes 47 that overlap each other along the longitudinal direction L. The holes 47 can be cylindrical, such that the first and second regions 43a and 43b can be arc-shaped as they extend along the longitudinal direction L. Each of the first and second regions 43a and 43b can be curved about a respective axis that extends along the transverse direction T, such that each of the first and second regions 43a and 43b define a curvature that is equal to the others of the first and second regions 43a and 43b, or can be different from one or more up to all of the others of the first and second regions 43a and 43b.

The nail body 32 further defines longitudinally opposed internal first and second end surfaces 49a and 49b, respectively, that are connected between the opposed longitudinal ends of the first and second internal surfaces 37a and 37b. Accordingly, the first and second internal surfaces 37a-b extend between the end surfaces 49a and 49b. The end surfaces 49a-b can each be curved about a respective axis that extends along the transverse direction T, such that the end surfaces 49a-b each define a curvature that can be the same as or different than the curvature of one or more up to all of the first and second regions 43a and 43b, respectively. The end surfaces 49a-b and the longitudinally outermost ones of the first and second internal surfaces 37a and 37b can cooperate so as to define a pair of longitudinal end pockets of the pockets 45, such as a longitudinally outermost pocket 52a of the pockets 45, and a longitudinally innermost pocket 52b of the pockets 45. The first and second regions 43a and 43b of the first and second internal surfaces 37a and 37b, respectively, define at least one longitudinally intermediate pockets 46 of the pockets 45 such as a plurality of longitudinally intermediate pockets 46, the intermediate pockets 46 disposed between the end pockets. Thus, at least one or both of the first and second internal surfaces 37a and 37b can define at least one intermediate pocket 46 such as a plurality of intermediate pockets 46 disposed between the end pockets along the longitudinal direction L.

The first and second internal surfaces 37a and 37b, and thus the compression slot 39, define a first width W1 that is measured along the lateral direction A. For instance, at least one of the first and second internal surfaces 37a and 37b defines at least one intersection 48 as described above, and the compression slot defines the first width W1 between the intersection 48 and the opposed one of the first and second internal surfaces. In accordance with one embodiment, the first and second internal surfaces can define opposed intersections 48, such that the first width A1 is defined between opposed ones of the intersections 48 along the lateral direction A along a direction substantially perpendicular to the longitudinal axis 31. For instance, the opposed intersections 48 can be disposed adjacent or between intermediate pockets 46, and can further be disposed between one of the intermediate pockets 46 and one of the end pockets as defined by the longitudinally outermost pocket 52a and the longitudinally innermost pocket 52b. The first and second internal surfaces 37a and 37b, and thus the compression slot 39, define a second width W2 that is measured along the lateral direction A (and is thus substantially parallel to the first widths W1) between opposed ones of the pockets 45, and intersects opposed ones of the first and second regions 43a and 43b at a location spaced from the respective intersections 48 along the longitudinal direction L. The second width W2 can thus extend along a direction parallel to the first width W1. In accordance with the illustrated embodiment, the first width W1 is less than the second width W2. In accordance with the illustrated embodiment, the first and second regions 43a and 43b are round and, for instance, arc-shaped, such that the second width W2 defines a diameter of a circle. The second width W2 can be equal to, less than, or greater than the respective diameters of the bone anchor holes 40.

While both internal surfaces 37a and 37b can define respective ones of the pockets 45 and intersections 48 in accordance with the illustrated embodiment, it should be appreciated in accordance with an alternative embodiment that only one of the surfaces 37a and 37b define the pockets 45 and intersections 48, while the other of the surfaces 37a and 37b can be devoid of pockets and intersections, and can extend substantially straight along the longitudinal direction or define any shape as desired. Therefore, the compression slot 39 can define the first width W1 that extends between the opposed surfaces 37a and 37b through at least one intersection 48, and can further define the second width W2 that extends between the opposed surfaces 37a and 37b through at least one pocket 45 along a direction parallel to the first width, such that the pockets 45 and intersections 48 are alternatingly arranged along the longitudinal direction L.

While the intersections 48 are positioned such that the first width W1 is substantially constant along the length of the compression slot 39 in accordance with the illustrated embodiment, it should be appreciated that the first width W1 can vary along the longitudinal direction L along the compression slot 39. Furthermore, when the second width W2 is define at a location of maximum lateral depth of the respective pockets 45, the second width W2 is substantially constant along the length of the compression slot 39 in accordance with the illustrated embodiment, though it should be appreciated that the second width W2 can alternatively vary along the longitudinal direction L along the compression slot 39. Varying one or both of the widths W1 and W2 along the compression slot 39 can produce increasing or decreasing biasing compression forces that are suitable to drive the compression member 53 along the compression slot 39, for instance when compressing the first and second bone segments 22 and 24 relative to each other so as to approximate the bone gap 26 as described in more detail below. In accordance with one embodiment, the difference between W2 and W1 can be within any range as desired, such as between and including a lower end of approximately 0.2 mm and an upper end of approximately 2.0 mm. For instance, the second width W2 can be sized as desired, and can be within the range between and including approximately 1.5 mm and approximately 10 mm. Furthermore, the first width W1 can be sized as desired, and can be within the range of approximately 1.3 mm and 9.8 mm. For example, when W2 is 1.5 mm, W1 may be 1.3 mm. In another example, when W2 is 10 mm, W1 may be 8 mm. In accordance with the illustrated embodiment, the length of each of the inner pockets 45 along the longitudinal direction can be defined as $2*[(W2/2)^2-(W1/2)^2]^{1/2}$. In accordance with the illustrated embodiment, the length of each of the outermost pockets 52a and 52b can be defined as $[W2/2-((W2/2)^2-(W1/2)^2)^{1/2}]$. The intramedullary nail 30 can define any suitable outer diameter along a direction substantially perpendicular to the longitudinal direction L as desired, such as less than 17.5 mm.

As described above, the compression slot 39 is defined by the nail body 32. For instance, in the embodiment illustrated in FIGS. 2A-D, the first and second internal surfaces 37a and 37b of the nail body 32 and first and second end surfaces 49a and 49b of the nail body 32 can be integral and monolithic with the nail body 32. Accordingly, the compression slot 39 can be defined by surfaces of the nail body 32 that are integral and monolithic with the nail body 32. Alternatively, referring now to FIGS. 2E-F, the nail body 32 can include an insert 61 that is removably attachable to one or both of the proximal and distal potions 34 and 36, respectively, of the nail body 32. The insert 61 can define at least one or more, such as all of, the first and second internal surfaces 37a and 37b and the first and second end surfaces 49a and 49b. Accordingly, the compression slot 39 can be carried by the insert 61. The nail body 32 can define an aperture 63 that extends at least into or through at least one or both of the first and second portions 33 and 35, respectively, of the nail body 32. The aperture 63 is sized to receive the insert 61 such that the compression slot 39 is carried by the respective one or both of the first and second portions 33 and 35 of the nail body 32. The insert 61 can be inserted into the corresponding aperture 63 so as to attach the insert 61 to the respective one or both of the first and second portions 33 and 35, respectively. Accordingly, the nail body 32 can include a pair of the inserts 61 that are carried by one or both of the proximal and distal portions 34 and 36, respectively, of the nail body 32.

Referring also to FIG. 3, the compression member 53 can be configured as an unthreaded nail or a threaded screw that can be configured as a bone anchor having a head 54 and a shaft 56 extending out from the head 54 along a central axis A. The shaft 56 can include threads 56a in accordance with the illustrated embodiment, or can alternatively be unthreaded, and can be shaped as desired, for instance cylindrical, and can be smooth and configured to move from and between the intermediate pockets 46 and the outer pockets 52a and 52b. The compression member 53 can be sized and shaped substantially identically with respect to a plurality of bone anchors 86 (see FIG. 10) that are sized to extend through the bone anchor holes 40 so as to fix the intramedullary nail 30 to the long bone 20. For instance, the compression member 53 can be selected from the plurality of bone anchors 86 so as to define a select one of the bone anchors 86. In accordance with the illustrated embodiment, the shaft 56 defines a maximum cross-sectional outer dimension D (which can be a diameter). For instance, the maximum cross-sectional outer dimension D can be measured along the lateral direction A between the internal surfaces 37a and 37b when the shaft 56 is disposed in the compression slot 39, such that the maximum cross-sectional outer dimension D is greater than the first width W1 of the compression slot 39. Accordingly, the intersection 48 disposed between first and second adjacent ones of the pockets 45 interferes with, and provides a resistance against, movement of the shaft 56 from the first one of the pockets 45 to the second one of the pockets 45. The resistance increases as the difference between the maximum cross-sectional outer dimension D and the first width W1 increases. As will be appreciated from the description below, an approximation force applied to the compression member 53 along the longitudinal direction L can be sufficient to overcome the resistance defined by interference between the intersections 48 and the shaft 56 so as to allow the compression member 53 to travel to adjacent pockets 45 of the compression slot 39. The maximum cross-sectional outer dimension D of the shaft 56 can be smaller or substantially equal to the second width W2 defined by the at least one pocket 45, such that the shaft 56 is sized to nest within the pockets 45. Alternatively, the cross-sectional distance D of the shaft 56 can be greater than the second width W2, but greater than W2 an amount that is less than the amount that the maximum cross-sectional outer dimension D of the shaft 56 is greater than the first width W1.

At least one or both of the shaft 56 and the internal surfaces 37a and 37b can be elastomeric, and thus temporarily elastically flexible so that the first width W1 is substantially equal to the cross-sectional dimension (e.g., diameter) of the shaft 56 so that the shaft 56 can translate from a first one of the pockets 45, past a corresponding intersection disposed between the first one of the pockets 45 and an adjacent second one of the pockets 45, and into the second one of the pockets 45. Furthermore, the internal surfaces 37a and 37b can be sloped (for instance curvilinearly as described above or substantially linearly), as they extend along the longitudinal directions so as to define the respective first and second regions 43a and 43b, respectively, so as to define a depth along the lateral direction as measured from an adjacent intersection 48. The depth of the first and second regions 43a-b can be at a maximum at their respective longitudinal midpoints, which can bisect the respective pockets 45. Thus, the pockets 45 can be deepest substantially at their longitudinal midpoints. Thus, the resistance of the first and second regions 43a and 43b against the compression member 53 can increase as the compression member 53 travels from one of the pockets 45 toward a corresponding intersection 48. The resistance can be at a maximum as the compression member 53 travels over the intersection, and can decrease (and can be negative so as to assist movement) as the compression member 53 travels from the intersection 48 into an adjacent pocket 45. In accordance with the illustrated embodiment, the internal surfaces 37a and 37b are resilient and elastically flexible away from each other, and the shaft 56 is substantially rigid. For instance, the compression member 53, and thus the shaft 56, can be made of any substantially rigid material as desired, including Titanium or other suitable stiff metals.

Figure 2G:
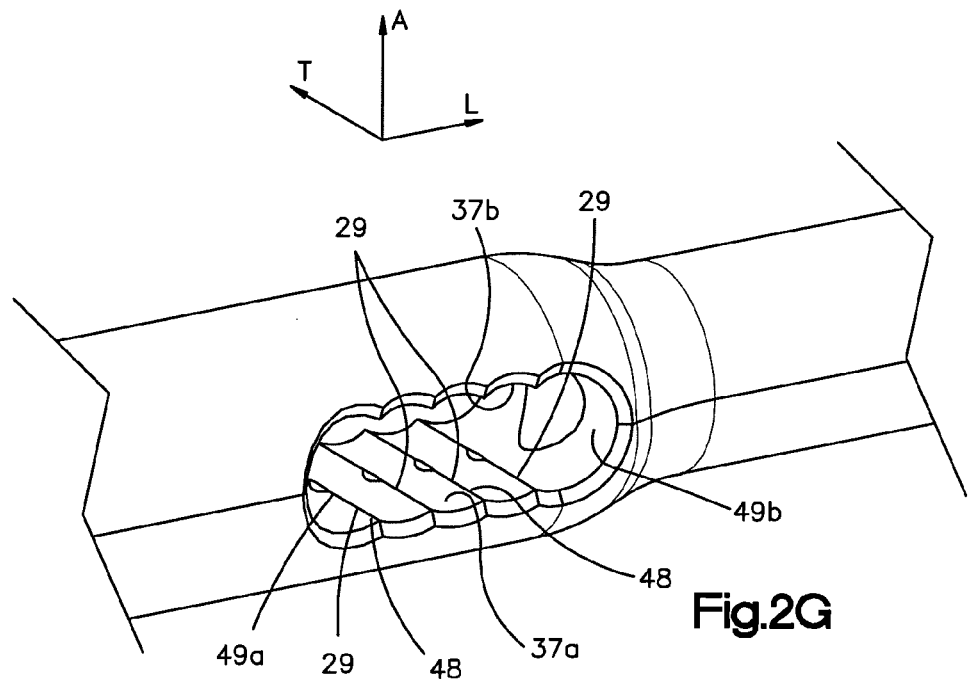
FIG. 2G is a perspective view of a portion of the intramedullary nail similar to the intramedullary nail illustrated in FIG. 2A, but wherein the compression slot as illustrated in FIG. 2A is partially defined by intersections constructed in accordance with an alternative embodiment.
Figure 2H:
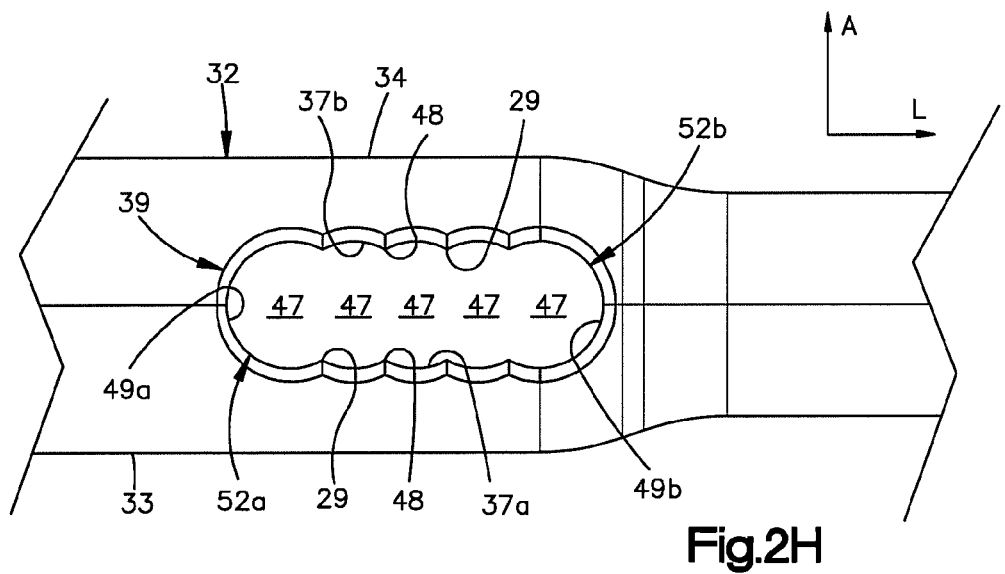
FIG. 2H is a top plan view the portion of the intramedullary nail illustrated in FIG. 2G.

As illustrated in FIGS. 2A-D, the internal surfaces 37a and 37b can converge at the intersections 48 such that the intersections define an edge 27 that is elongate along the transverse direction T. Thus, the intersections 48 can be substantially V-shaped. It should be appreciated, however, that the intersections 48 can define any suitable size and shape as desired. For instance, as illustrated in FIGS. 2G-H, the intersections 48 can define surfaces 29 that are elongate along the transverse direction T, and further extends along a length of the respective internal surfaces 37a-b along the longitudinal direction L. The surfaces 29 can be substantially straight along the longitudinal direction L, or can be curved as they extend along the longitudinal direction L. It should be appreciated that one or more of the intersections 48 can define edges 27, and alternatively or additionally one or more of the intersections 48 can define surfaces 29.

Figure 7A:
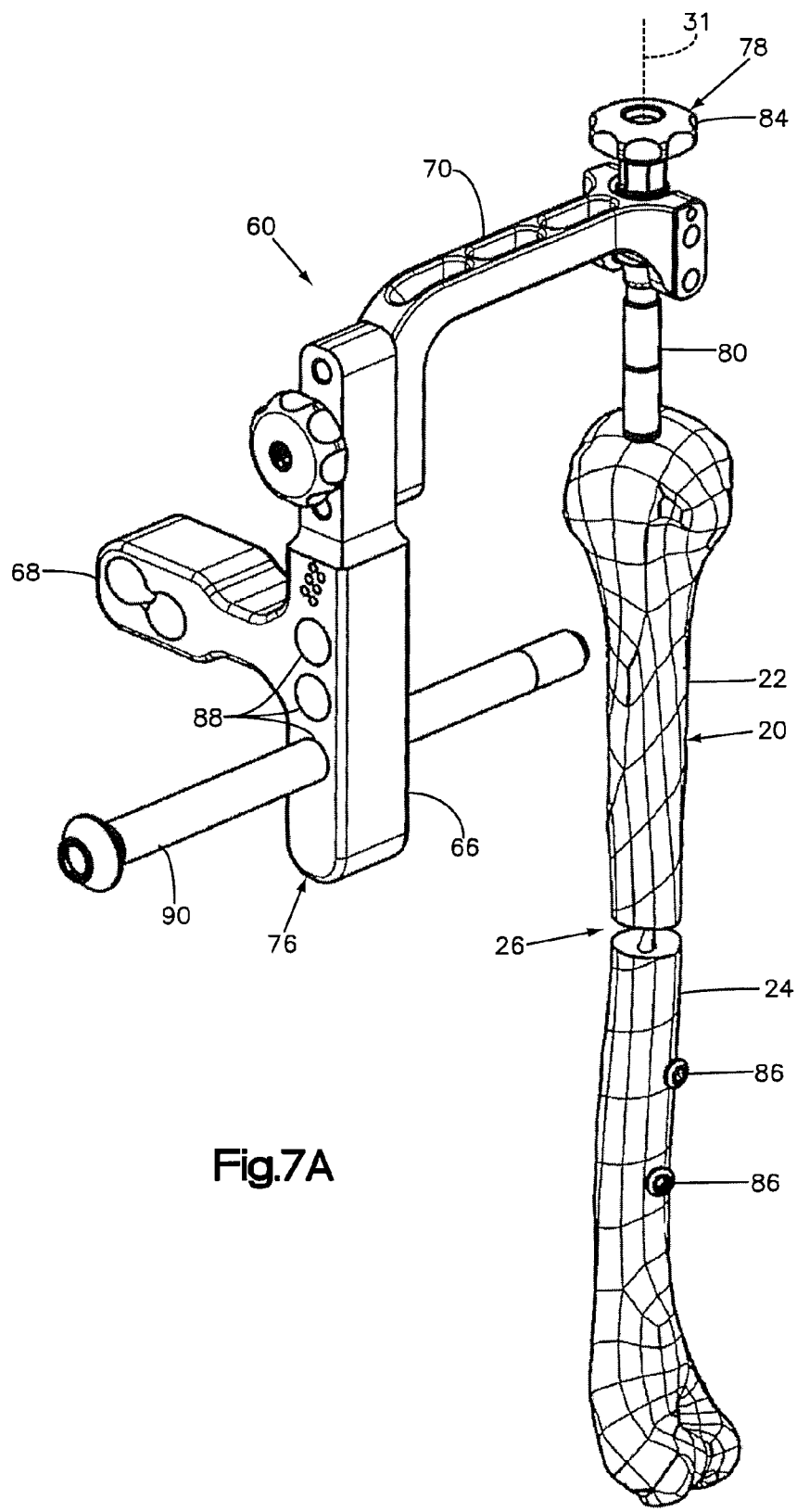
FIG. 7A is a perspective view of the fixation system illustrated in FIG. 6, but showing the implantation assembly including an aiming sleeve coupled to the support frame and operatively aligned with the compression slot of the intramedullary nail.
Figure 7B:
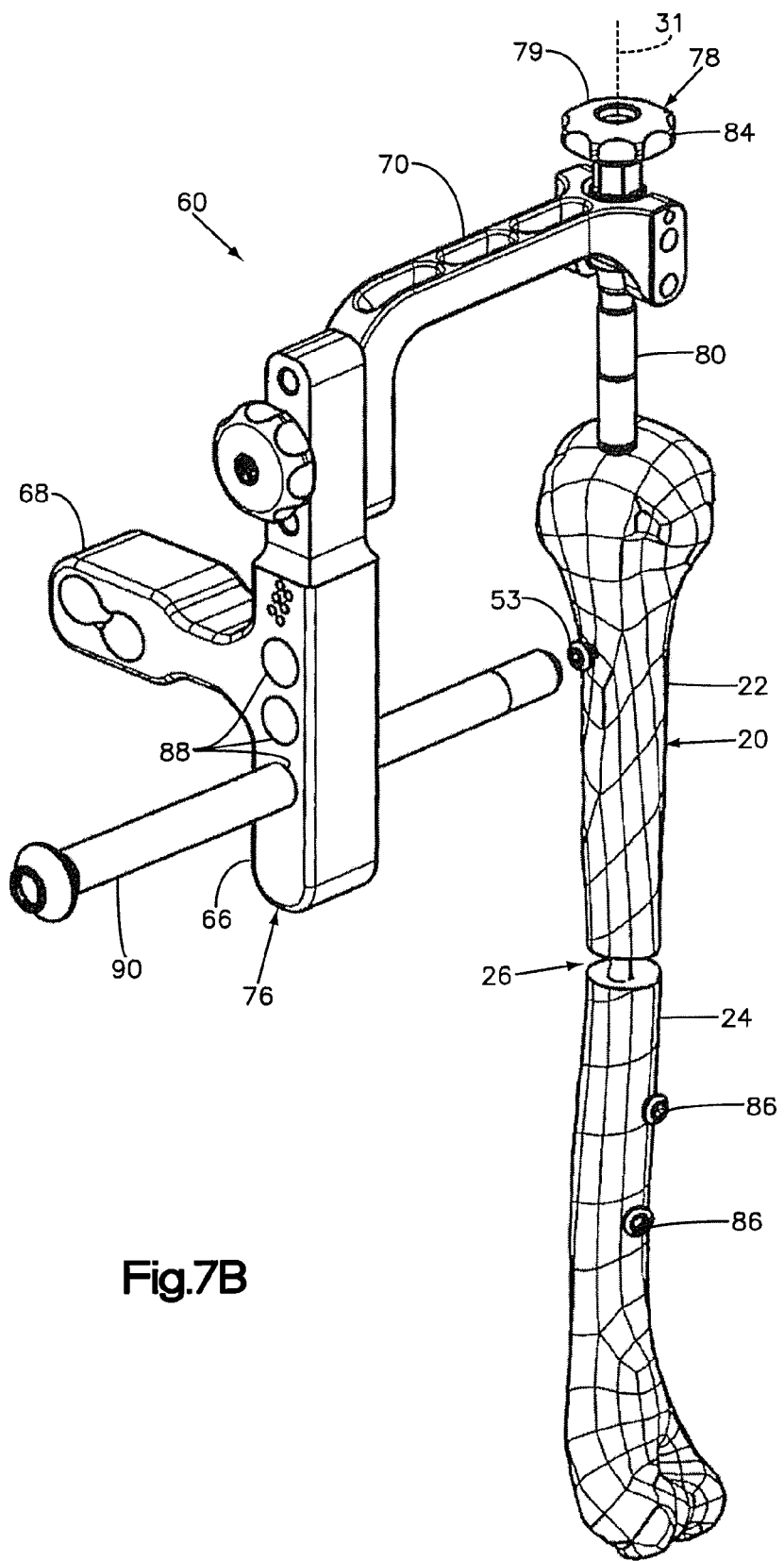
FIG. 7B is a perspective view of the fixation system illustrated in FIG. 7A, but showing the bone fixation assembly including a compression member configured as a bone screw inserted into the proximal bone segment and into the compression slot.
Figure 7C:
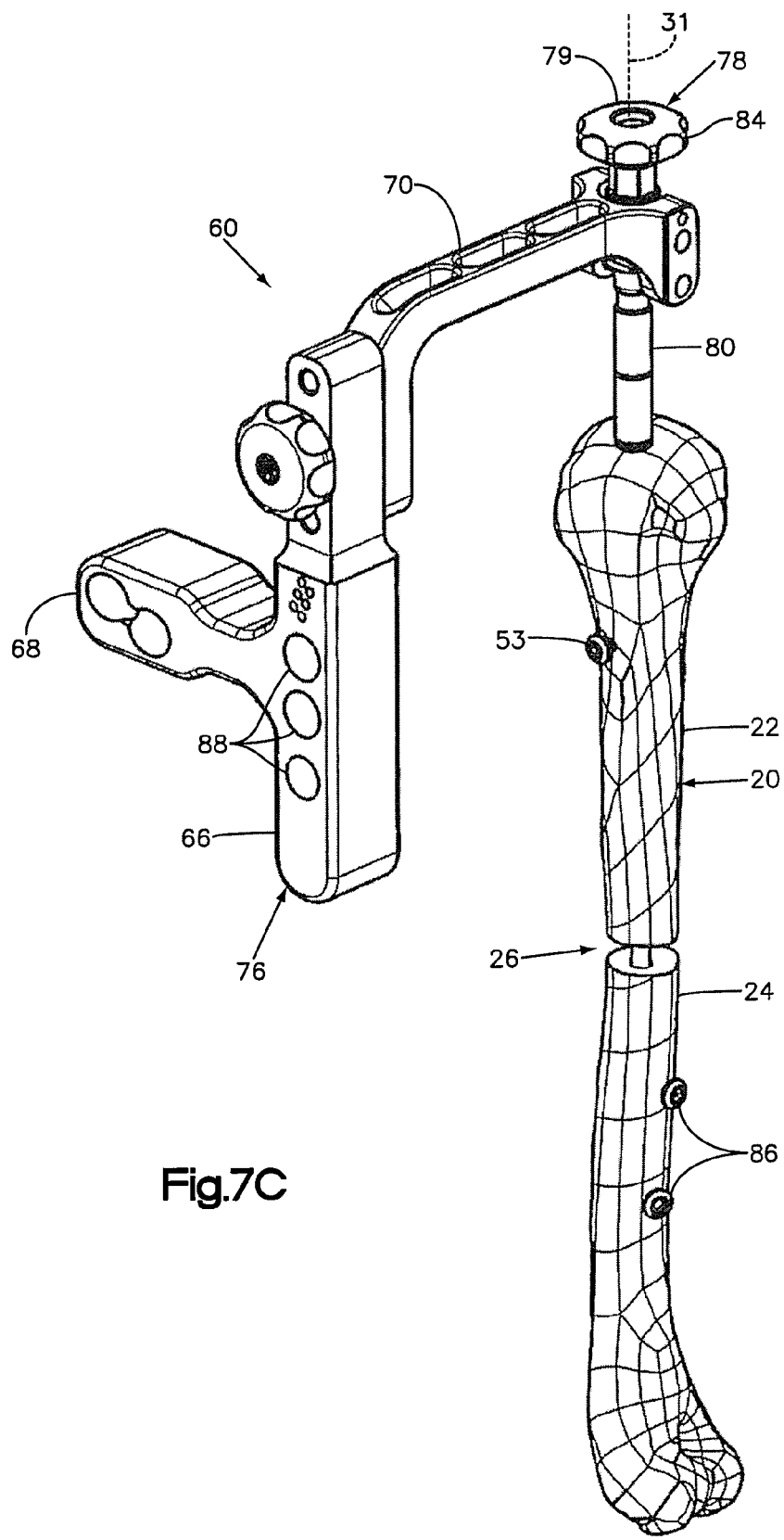
FIG. 7C is a perspective view of the fixation system illustrated in FIG. 7B, but showing the aiming sleeve removed.

Referring again to FIGS. 2A-D and FIG. 4B, the nail body 32 can further include an engagement member 58 that is configured to removably attach to a complementary engagement member 82 of a brace member 78 (see FIG. 7A) that is configured to support the intramedullary nail 30, such that a compression actuator 92 (see FIG. 8A) that is movable relative to the brace member 78 is configured to apply the approximation force to the compression member 53 that causes the compression member 53 to translate along the compression slot 39. In accordance with the illustrated embodiment, the engagement member 58 can be configured as a bore 57 that is defined by the intramedullary nail 30 and extends along the longitudinal direction L into the longitudinally outer terminal end of the first portion 33 of the nail body 32. Accordingly, in accordance with the illustrated embodiment, the engagement member 58 defines a bore 57 that extends distally into the outer terminal end (e.g., the proximal end) of the proximal portion 34 of the nail body 32. In accordance with an alternative embodiment, the compression slot 39 can be defined in the distal portion 36 of the nail body 32, and the bore 57 can extend proximally into the longitudinally outer end (e.g., the distal end) of the distal portion 36. The nail body can define internal threads 59 that circumscribe the bore 57 can be threaded so as to mate with the threads of the complementary engagement member of the brace member 78.

Figure 4B:
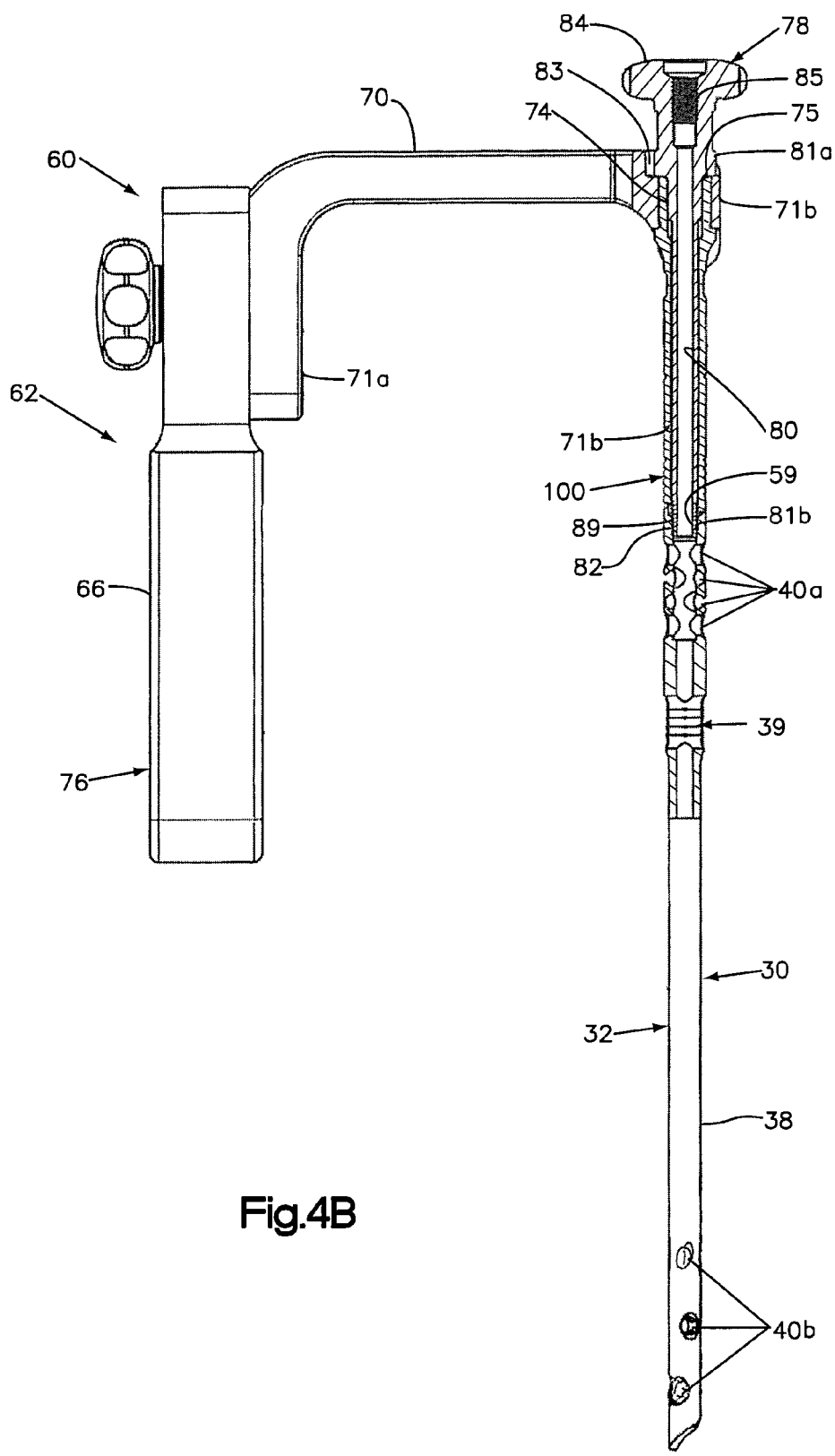
FIG. 4B is a sectional side elevation view of the fixation system illustrated in FIG. 4A, with a portion cut away.
Figure 5:
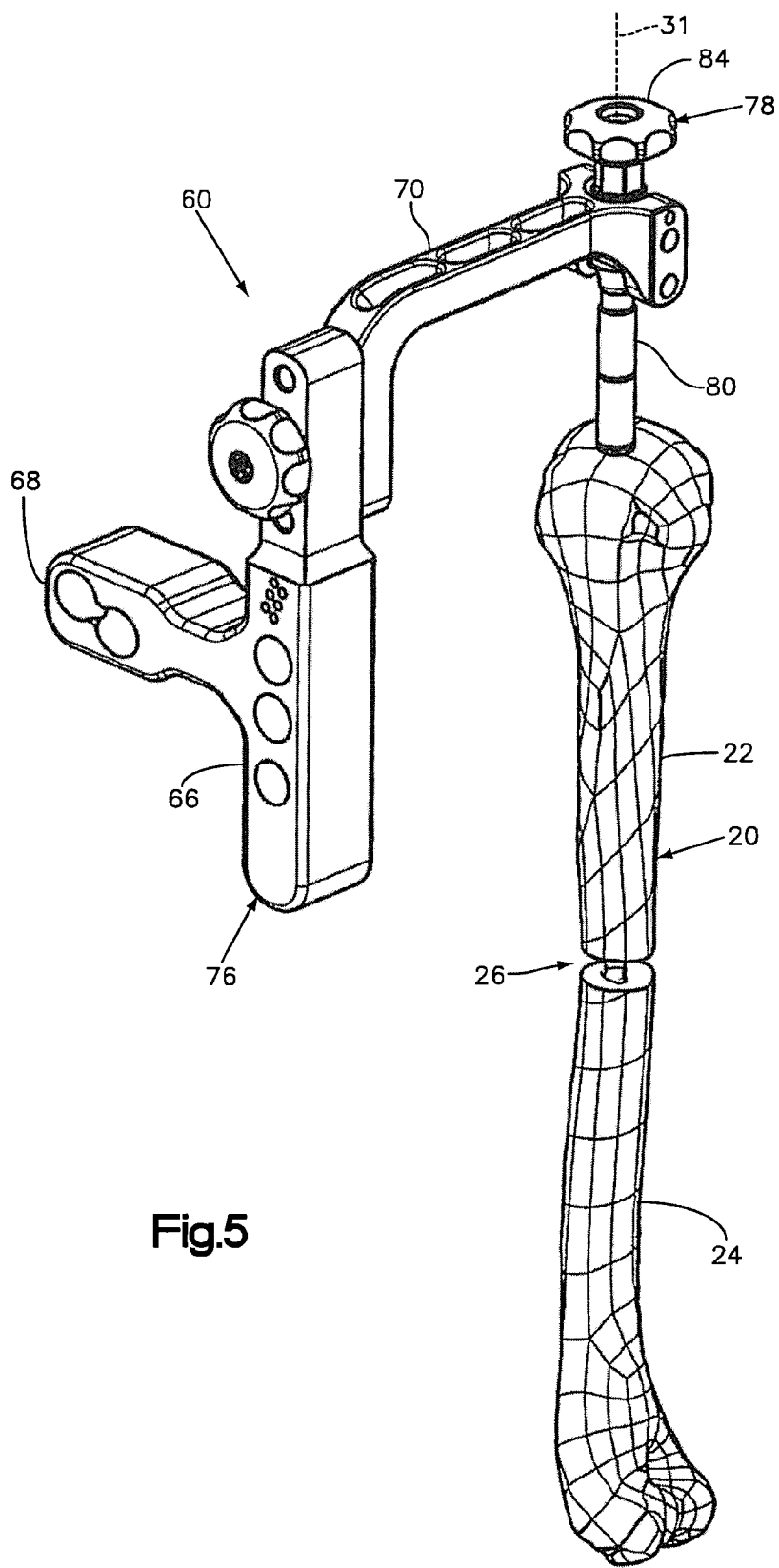
FIG. 5 is a perspective view of the fixation system illustrated in FIG. 4, showing the intramedullary nail implanted in the medullary canal of the fractured long bone illustrated in FIG. 1.

Referring also to FIGS. 4A-B, a bone fixation system 60 can include an implantation assembly 62 and a bone fixation assembly 64. The bone fixation assembly 64 can include the intramedullary nail 30, the compression member 53 (see FIG. 3), and a plurality of bone anchors 86 (see FIG. 10) that are configured to extend through the bone anchor holes 40 so as to fix the intramedullary nail 30 to the fractured long bone 20. The implantation assembly 62 can include a support frame 76, one or more aiming sleeves 90 (see FIG. 7A), the brace member 78, and can further include the compression actuator 92 (see FIG. 8A). A kit can thus be provided that includes at least one such as a plurality of any one up to all of the components of the bone fixation system 60, such that the kit can include components of the bone fixation system 60, such as the intramedullary nail 30, constructed of different sizes and shapes.

With continuing reference to FIGS. 4A-B, the support frame 76 includes an alignment body 66 that is elongate along the longitudinal direction L, a handle 68 that extends out from the alignment body 66 along a first direction that can be angularly offset, for instance, perpendicular to, the longitudinal direction, and a support arm 70 that extends out from the alignment body 66 along a direction angularly offset, for instance substantially perpendicular, to the longitudinal direction. The support arm 70 can extend from the alignment body 66 along an opposite direction with respect to the direction that the handle 68 extends from the alignment body 66. The alignment body 66 includes at least one, such as a plurality of attachment locations 72 that are longitudinally spaced from each other and each configured to attach to the support arm 70, for instance at a proximal end 71a of the support arm 70, such that the support arm 70 can be attached to the alignment body 66 at a select one of a plurality of longitudinally spaced attachment locations 72. For instance, the attachment locations 72 can be configured as apertures that extend into or through the alignment body 66 and are sized to receive a coupler 73, such as a knob, that is configured to selectively extends into or through the attachment locations and secure to the proximal end 71a of the support arm to thereby fix the support arm 70 to the alignment body 66 at one of the attachment locations 72. Because the attachment locations 72 are spaced from each other in the longitudinal direction, and because the support arm 70 is configured to support the intramedullary nail 30 at its distal end 71b, the attachment location 72 to which the support arm 70 is mounted can at least partially determine a longitudinal position of the intramedullary nail relative to the support frame 76.

In accordance with the illustrated embodiment, the support arm 70 includes an engagement member that is configured to support the brace member 78 so as to retain the intramedullary nail 30 at a predetermined location relative to the alignment body 66. For instance, the engagement member of the support arm 70 can be configured as an aperture 74 that extends longitudinally through the distal end 71b of the support arm 70 and is sized so as to receive the brace member 78. The support arm 70 can define a shoulder 75 that defines the aperture 74 and provides a seat configured to support the brace member 78.

With continuing reference to FIGS. 4A-B, the brace member 78 includes a longitudinally elongate shaft 80 that extends through the distal end 71b of the support arm 70, and defines a first proximal end 81a and an opposed second distal end 81b that is distally spaced from the first proximal end 81a substantially along the longitudinal direction L. The brace member 78 can include an engagement member at its distal end 81b that is configured to be secured to the engagement member 58 of the intramedullary nail 30. In particular, the brace member 78 includes, for instance at the distal 81b end of the brace member 78, an engagement member 82 that can be configured as external threads 89 that mate with the internal threads 59 of the bore 57 of the intramedullary nail 30 so as to removably attach the intramedullary nail 30 to the brace member 78. The brace member 78 is thus configured to removably secure the intramedullary nail 30 to the support frame 76 by mating the threads 89 of the engagement member 82 with the threads 59 of the intramedullary nail 30.

The brace member 78 can include a knob 84 at that is attached to the proximal end 81a of the shaft 80. For instance, the knob 84 can be integral and monolithic with the shaft 80, or can be discreetly attached to the shaft 80, such that the knob 84 is rotatably coupled to the shaft 80 about an axis that extends in the longitudinal direction L. For instance, as the knob 84, and thus the shaft 80, are rotated along a first direction relative to the intramedullary nail 30, the threads 89 of the brace member 78 purchase with the threads 59 of the nail body 32 so as to secure the brace member 78 to the intramedullary nail 30. As the knob 84, and thus the shaft 80, are rotated along a second direction opposite the first direction relative to the intramedullary nail 30, the threads 89 of the brace member 78 purchase with the threads 59 of the nail body 32 so as to remove the brace member 78 from the intramedullary nail 30.

The brace member 78 further includes a second engagement member that is configured to attach to the engagement member of the support arm 70. The knob 84 of the brace member 78 can define an internal shoulder 83 that is configured to rest against the shoulder 75 of the support arm 70 so as to secure the brace member 78 to the support frame 76 with respect to distal movement along the longitudinal direction L relative to the support frame 76. It should be appreciated that the brace member 78 can be coupled to the support frame 67 using any suitable alternative connection as desired.

The intramedullary nail 30 can define a terminal end that defines a tip 41 at one or both of the longitudinally outer ends of the first and second portions 33 and 35 of the nail body 32. In accordance with the illustrated embodiment, the tip 41 extends from the outer end of the second portion 35 of the nail body 32. For instance, in accordance with the illustrated embodiment, the tip 41 is disposed at the longitudinally distal end of the distal portion 36 of the nail body 32 when the proximal portion 34 of the nail body 32 defines the compression slot 39. The tip 41 is configured to be driven into the long bone 20 substantially along the longitudinal direction L. In accordance with the illustrated embodiment, the tip 41, and thus the intramedullary nail, can be driven into the proximal bone segment 22, for instance through the head of the long bone 20, and into the medullary canal 23 of the long bone (see FIG. 1) such that the proximal portion 34 of the nail body 32 is disposed in the medullary canal 23 of the proximal bone segment 22, the distal portion 36 of the nail body 32 is disposed in the medullary canal 23 of the distal bone segment 24, and the intermediate portion 38 extends across the bone gap 26. The support arm 70 can define a plurality of visualization windows that extend into or through the distal end 71b so as to aid so as allow a visual determination of the depth of the intramedullary nail 30 in the long bone 20.

Figure 6:
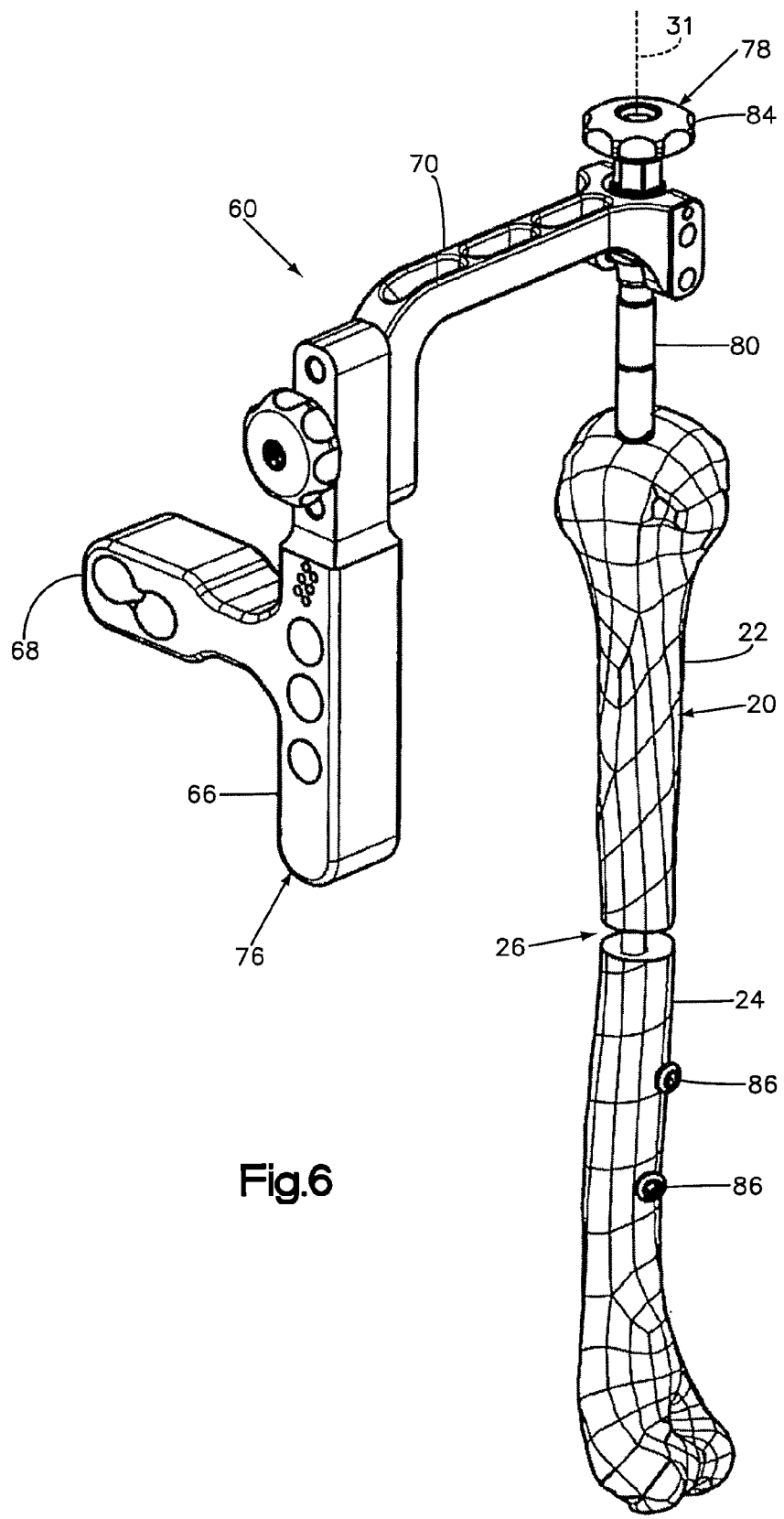
FIG. 6 is a perspective view of the fixation system as illustrated in FIG. 5, but showing the bone fixation assembly including a plurality of bone fixation screws inserted into the distal bone segment and respective distal bone anchor holes of the intramedullary nail so as to fix the distal portion of the intramedullary nail to the distal bone segment.

Referring to FIGS. 2A-B and FIG. 6, the second portion 35 of the nail body 32 can be fixed to the respective bone segment of the fractured long bone 20. In accordance with the illustrated embodiment, the proximal portion 34 of the nail body 32 defines the compression slot 39 and the distal portion 36 of the nail body 32 is fixed to the distal bone segment 34. For instance, at least one bone anchor 86, such as a plurality of bone anchors 86, can be inserted into the distal bone segment 24 and into or through respective ones of the plurality of second bone anchor holes 40b so as to fix the distal bone segment 24 to the second 35 of the nail body 32 with respect to relative motion, and in particular with respect to relative translation along the longitudinal direction L. In accordance with the illustrated embodiment, a pair of bone anchors 86, which can be configured as bone screws, can be inserted into or through a respective pair of the plurality of second bone anchor holes 40b. The bone anchors 86 can be inserted through any suitable aiming sleeve aligned with the second bone anchor holes 40b using an aiming arm or any suitable system configured to align the bone anchors 86 with the second bone anchor holes 40b and drive the bone anchors 86 into the fractured long bone 20 and into the second bone anchor holes 40b. It should be appreciated that once the second bone anchor holes have been driven into the distal bone segment 24 and into respective ones of the second bone anchor holes 40b, the distal bone segment 24, the intramedullary nail 30, and the brace member 78 are all fixed to each other with respect to relative translation along the longitudinal direction.

Referring now to FIGS. 2A-3, and FIGS. 7A-C, once at least one of the bone anchors 86 has attached the second portion 35 of the nail body 32 to a first one of the proximal and distal bone segments 22 and 24, such as the distal bone segment 24 as illustrated, the compression member 53 can be inserted into other of the first and second bone segments 22 and 24, such as the proximal bone segment 22, that is aligned with the compression slot 39, and further inserted into or through the compression slot 39. It should be appreciated that the compression member 53 can alternatively be driven into the long bone 20 and further inserted into or through the compression slot 39 before the at least one bone anchor 86 has attached the second portion 35 of the nail body 32 to the long bone 20. Accordingly, the compression member 53 can initially be driven into the distal bone segment 24 and into a select pocket 45, such that the compression slot 39 defines at least one other pocket 45 that is disposed distal of the select pocket (e.g., along a direction from the first portion 33 of the nail body 32 toward the second portion 35 of the nail body 32), and spaced from the select pocket any longitudinal distance as desired, such as a distance at least substantially equal to the bone gap distance D1.

In accordance with the illustrated embodiment, the support frame 76 defines at least one guide aperture 88 such as a plurality of guide apertures 88 that are spaced along the alignment body 66 in the longitudinal direction L and sized to receive the aiming sleeve 90, which can be cannulated and positioned in a desired guide aperture 88 so as to be operably aligned with a select one of the pockets 45 of the compression slot 39, such that at least one pocket 45 is disposed longitudinally inward of the select pocket 45. In accordance with the illustrated embodiment, the select pocket 45 can be the longitudinally outermost pocket 52a or any of the intermediate pockets 46 as desired. When the first portion 33 of the nail body 32 is the proximal portion 34 as illustrated, the longitudinally outermost pocket 52a is a proximal-most pocket. If the first portion 33 of the nail body 32 is the distal portion 36 in accordance with an alternative embodiment, the longitudinally outermost pocket 52a is a distal-most pocket. In accordance with one embodiment, the aiming sleeve 90 can be aligned with the select pocket 45 such that the distance between the select pocket 45 and the innermost pocket 52b along the longitudinal direction is at least equal to the bone gap distance D1 (see FIG. 1), such that movement of the compression member 53 in the compression slot 39 along the longitudinal direction can reduce the bone gape distance D1 to approximately zero.

Figure 8A:
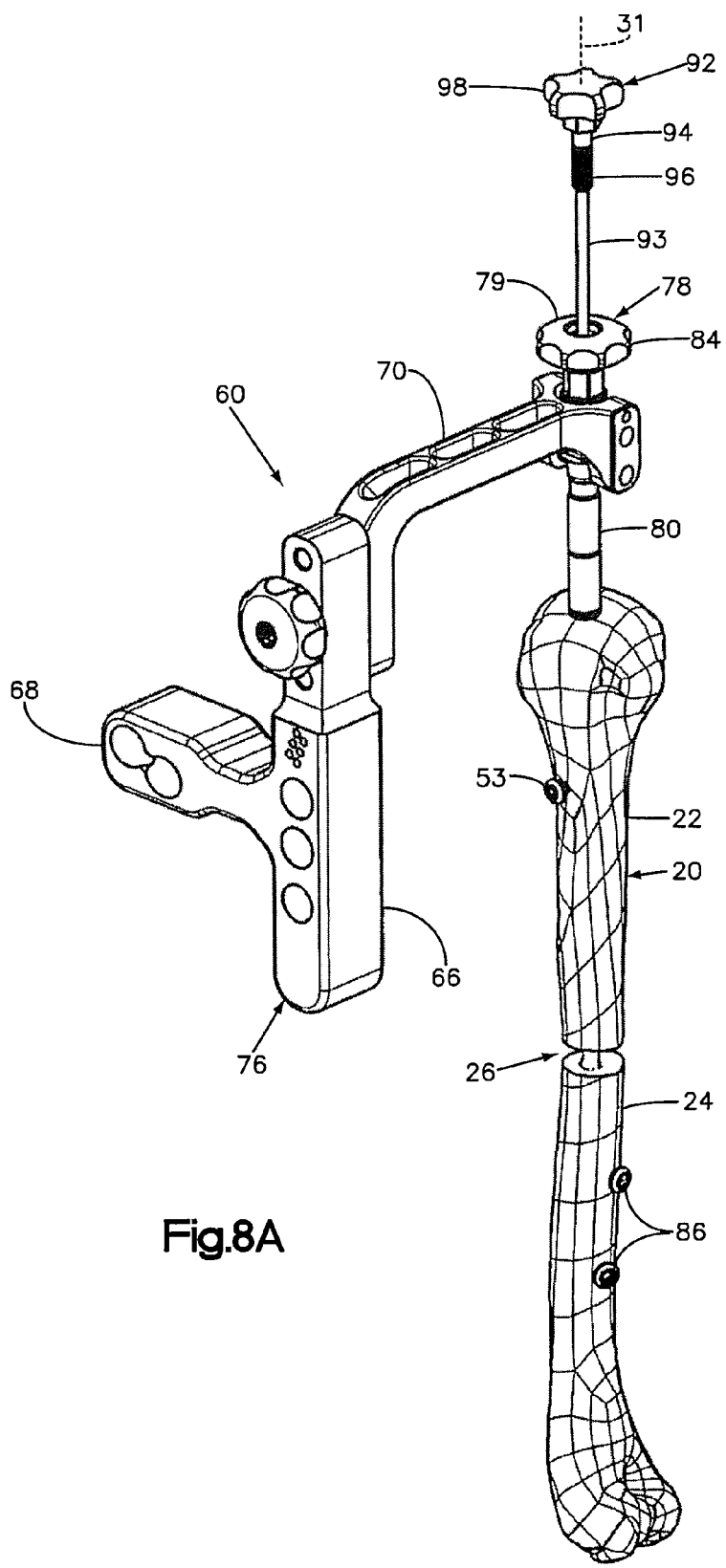
FIG. 8A is a perspective view of the fixation system illustrated in FIG. 7C, but showing the implantation assembly including a compression actuator aligned with the compression member.
Figure 8B:
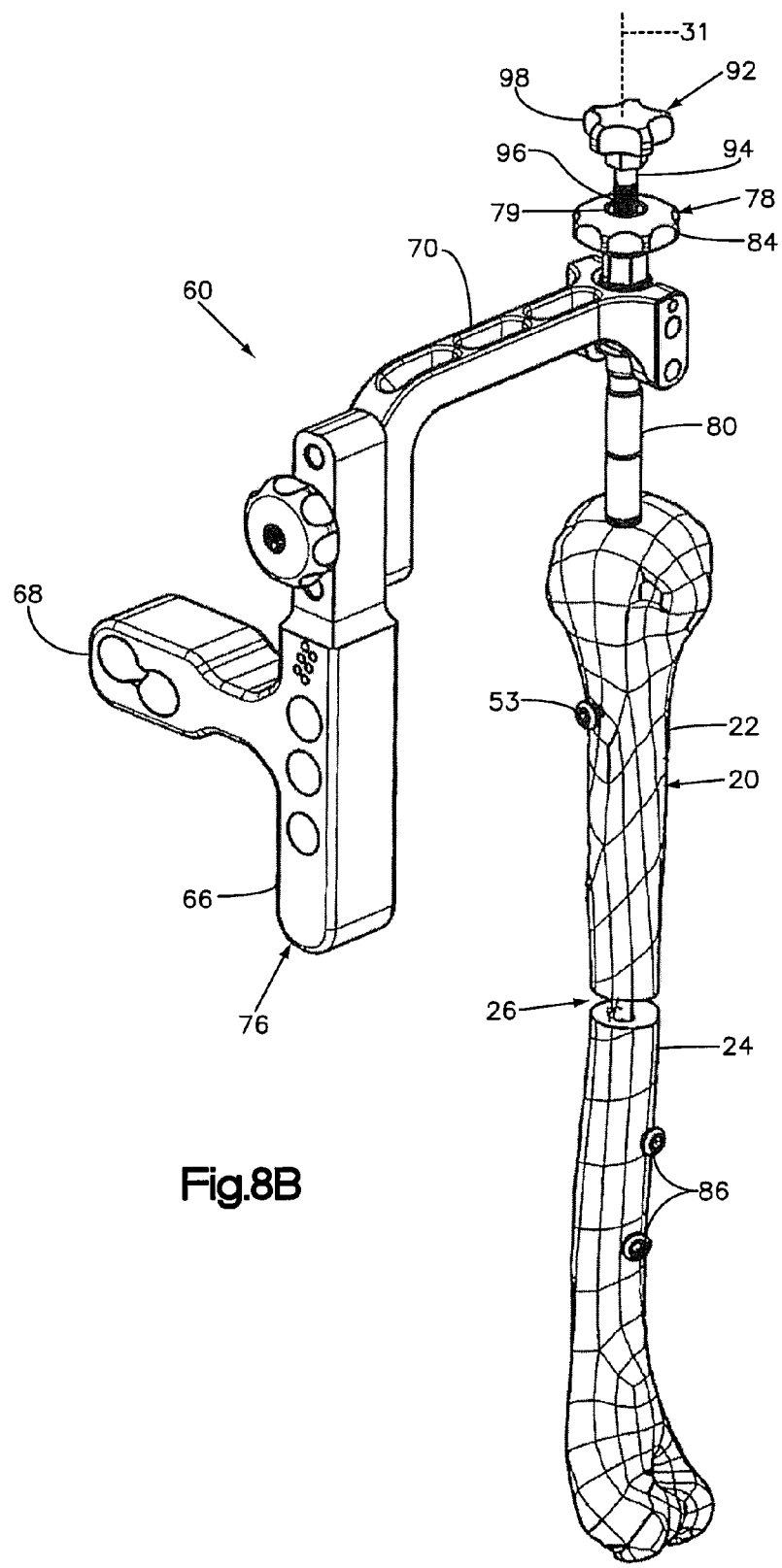
FIG. 8B is a perspective view of the fixation system illustrated in FIG. 8A, but showing the compression actuator operatively coupled to the support frame.
Figure 8C:
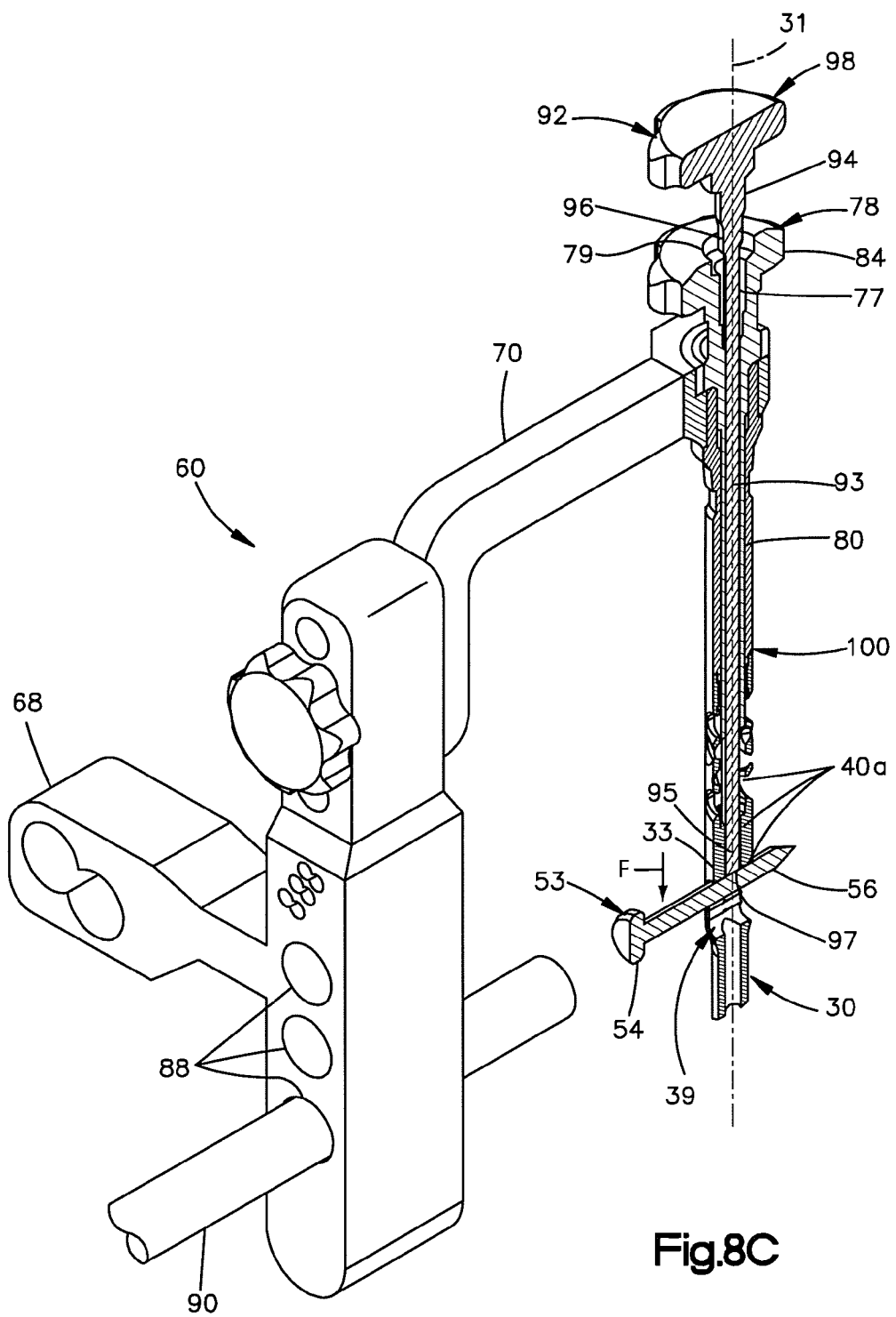
FIG. 8C is a perspective view of the fixation system illustrated in FIG. 8B, showing portions in cross-section.

Referring also to FIGS. 8A-C, once the aiming sleeve 90 is aligned with the select pocket 45, the compression member 53 can be driven into the bone segment that is aligned with the first portion 33 of the nail body 32. In accordance with the illustrated embodiment, the compression member 53 is driven into the proximal bone segment 22 and into or through the select pocket 45, which can be the longitudinally outermost pocket 52a or one of the intermediate pockets 46. The aiming sleeve 90 can then be removed from the support frame 76 such that the compression member 53 is at least temporarily or permanently fixed to the proximal bone segment 22 and inserted into the compression slot 39. Thus, the compression member 53 is fixed to the proximal bone segment 22 with respect to translation in the longitudinal direction.

Once the compression member 53 has been inserted into the proximal bone segment 22 and the compression slot 39, and the distal bone segment 24 has been fastened to the distal portion 36 of the nail body 32 with respect to relative longitudinal movement, the compression actuator 92 can be operatively engaged with the compression member 53 and subsequently moved relative to the brace member 78, and thus the nail body 32 and distal bone segment 24, from a first position to a compressed position. The compression actuator 92 is configured to operatively engage the compression member 53 such that movement of the compression actuator 92 along the longitudinal direction L, for instance toward the bone gap 26, which can define the distal direction as illustrated, causes the compression member 53 to likewise translate along with the proximal bone segment 22 toward the distal bone segment so as to approximate the bone gap 26.

In accordance with the illustrated embodiment, the compression actuator 92 can include a shaft 93 having a proximal end 94 and a distal end 95 that is spaced from the proximal end 94 along the longitudinal direction L. The compression actuator 92 can include an engagement member, for instance threads 96, that are carried by an external surface of the shaft 93. The brace member 78 can carry a complementary engagement member, such as threads 77 that mate with the threads 96 of the compression actuator 92 so as to removably attach the compression actuator 92 to the brace member 78, and thus also to the support frame 76, such that the compression actuator 92 is movable with respect to the intramedullary nail 30. For example, the brace member 78 can define a cannulation 79 that can extend through one or both of the knob 84 and the shaft 80, and can present the internal threads 77 that are configured to mate with the external threads 96 of the compression actuator 92. The shaft 93 of the compression actuator 92 can extend along the longitudinal direction L a distance that is greater than that of the shaft 80 of the brace member 78 and the cannulation 79, such that the shaft 93 can be inserted through the cannulation 79 so that at least the distal end 95 of the compression actuator 92 extends longitudinally out the brace member 78. The compression actuator 92 can include a knob 98 that extends proximally from the shaft 93. For instance the knob 98 can be integral and monolithic with the shaft 93, or can be discreetly attached to the shaft 93, such that the knob 98 is coupled to the shaft 93 with respect to relative rotation about an axis that extends in the longitudinal direction L.

Accordingly, rotation of the compression actuator 92 in a first direction, which can also be referred to as an engagement direction, relative to the brace member 78 causes the threads 96 to purchase with the threads 77 so as to secure the compression actuator 92 to the brace member 78. Rotation of the compression actuator 92 in a second direction, which can be referred to as a disengagement direction that is opposite the first direction, relative to the brace member 78 causes the threads 96 to purchase with the threads 77 so as to remove the compression actuator 92 from the brace member 78. It should be appreciated that rotation of the compression actuator 92 in the first direction relative to the brace member 78 causes the compression actuator 92 to advance relative to the nail body 32 along the longitudinal direction L from the first portion 33 of the nail body 32 toward the second portion 35 of the nail body, which defines a distal direction in accordance with the illustrated embodiment. Rotation of the compression actuator 92 in the second direction relative to the brace member 78 causes the compression actuator 92 to retract relative to the nail body 32 along the longitudinal direction L from the second portion 35 of the nail body 32 toward the first portion 33 of the nail body, which defines a proximal direction in accordance with the illustrated embodiment. Thus, the compression actuator 92 can be removably coupled to the brace member 78, and can be removably fixed to the compression member 53 with respect to distal translation in the longitudinal direction L.

The compression actuator 92 is attached to the brace member 78 so as to be movable longitudinally relative to the support frame 76, the intramedullary nail 30, and the distal bone segment 24 that is fixed to the second portion 35 of the intramedullary nail 30. It should be appreciated that the compression actuator 92 can be attached to the brace member 78 so as to translate along the longitudinal direction L relative to the brace member 78, and thus the support frame 67 and intramedullary nail 30, in any alternative manner as desired. For instance, in accordance with one embodiment, the compression actuator 92 can be movably connected to the brace member 78, and thus the support frame 76 and the intramedullary nail 30, by a rack-and-pinion such that rotation about an axis substantially perpendicular to the longitudinal direction L causes the compression actuator 92 to translate distally with respect to the brace member 78 and the intramedullary nail 30. Alternatively still, a distal translation force applied to the compression actuator 92 can cause the compression actuator 92 to translate distally relative to the brace member 78 and the intramedullary nail 30.

The distal end 95 of the compression actuator 92 defines an engagement member that can be configured as an abutment surface 97 that is at least partially aligned with the compression member 53 along the longitudinal direction L as the compression actuator 92 is attached to the brace member 78 and moves distally with respect to the brace member 78. As a result, distal translation of the compression actuator 92 relative to the brace member 78 causes the abutment surface 97 of the distal end 95 of the compression actuator 92 to contact the compression member 53, and further rotation of the compression actuator 92 relative to the brace member 78 causes the abutment surface 97, and thus the distal end 95 of the compression actuator 92, to apply a compressive biasing force to the compression member 53 that urges the compression member 53 to translate along the compression slot 39 in a direction from the first portion 33 of the nail body 32 toward the second portion 35 of the nail body 32, which can be distally as illustrated, so as to compress the proximal and distal bone segments 22 and 24, respectively, and approximate the bone gap 26.

The abutment surface 97 can integral and monolithic with respect to the shaft 93, or can be discretely attached to the shaft 93 or any other part of the compression actuator 92. For instance, the abutment surface 97 can be rotatable with respect to one or both of the knob 98 and shaft 93, such that as the compression actuator 92 rotates, the abutment surface 97 can remain stationary with respect to rotation as it applies the biasing force to the compression member 53. For instance, the abutment surface can be rotatable with respect to the shaft 93. Alternatively or additionally, the shaft 93 can be rotatable with respect to the knob 98. Alternatively still, the abutment surface 97 can rotate along with the knob 98 as it applies the biasing force to the compression member 53. Thus, the compression actuator 92 is configured to apply a biasing force to the compression member 53 that is greater than a retention force applied to the compression member 53 by the mechanical interference between the compression member 53 and the internal surfaces 37a and 37b, for instance at the intersections 48. Accordingly, the biasing force can define an approximation force that causes the compression member 53 to travel along the scalloped compression slot 39.

Figure 8D:
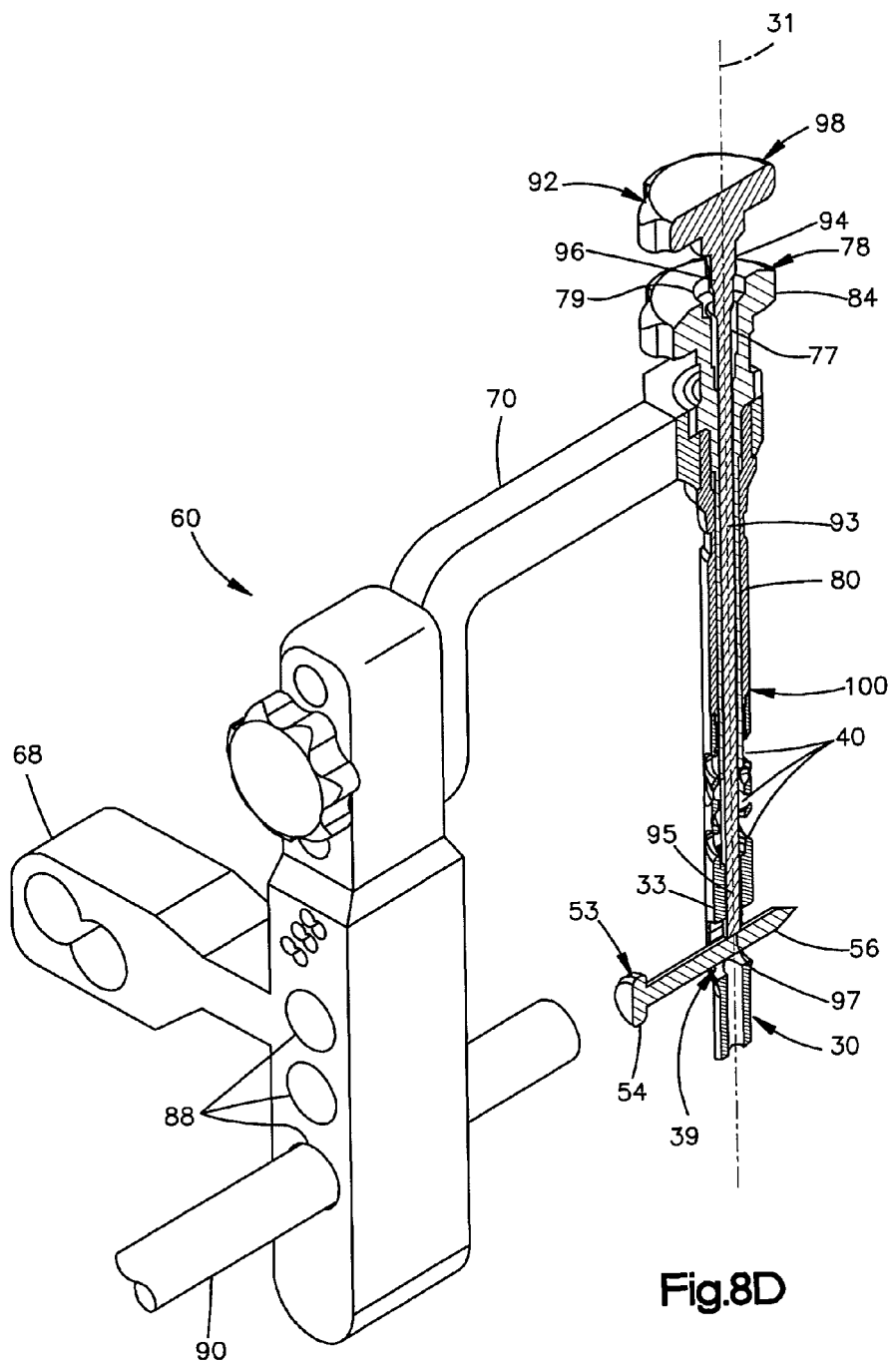
FIG. 8D is a perspective view of the fixation system illustrated in FIG. 8C, but showing the compression actuator in a compressed position that moves the compression member along the compression slot so as to approximate the bone gap.

As described above, the internal surfaces 37a and 37b are sloped along a direction from the pockets 45, for instance at the longitudinal the midpoint of the pockets 45, toward the adjacent intersection 48. Furthermore, the width W1 between the adjacent internal surfaces 37a and 37b is less than the cross-sectional distance of the shaft 56 of the compression member 53. Accordingly, the internal surfaces 37a and 37b provides a reactive resistance force to the compression member 53 that is opposite the compressive biasing force F of the compression actuator 92 as the biasing force F urges the compression member 53 toward the intersection 48, for instance from the midpoint of the corresponding pocket 45. When the biasing force F of the compression actuator 92 reaches an approximation force that is at level greater than the resistance force of the compression member 53, for instance as the compression actuator 92 is further rotated relative to the brace member 78, at least one or both of the shaft 56 of the compression member 53 and the internal surfaces 37a and 37b can deform, thereby temporarily decreasing the maximum cross-sectional outer dimension D of the shaft 56 (FIG. 3) and/or temporarily increasing the width W1 of the intersection 48 (FIG. 2C), until the maximum outer cross-sectional dimension D of the shaft 56 is substantially equal to the width W1 of the intersection 48. For instance, one or both the shaft 56 and the internal surfaces 37a and 37b can elastically deform as the compression member 53 travels along the compression slot 39. Alternatively, one or both of the shaft 56 and the internal surfaces 37a and 37b can plastically deform as the compression member 53 travels along the compression slot 39. Accordingly, once the compression actuator 92 translates along the longitudinal direction L and is brought into engagement with the compression member, further translation of the compression actuator 92 with respect to the intramedullary nail 30 causes the abutment surface 97 apply the approximation force F to the compression member 53 that causes the compression member 53 to ratchet along sequential pockets 45 of the compression slot 39 against the resistive force, as illustrated in FIGS. 8C-D. In accordance with one embodiment, for instance when the long bone 20 is a humerus bone, the approximation force can be approximately 100N. When the long bone 20 is a femur, the compression force can go up to approximately 500N. When the long bone 20 is a tibia, the approximation force can be between approximately 100N and approximately 500N. Thus, the approximation force can be within the range of approximately 100N and approximately 500N.

In accordance with the illustrated embodiment, as the shaft 56 travels along the intersections 48 from a first one of the holes 47 into a second one of the holes 47 that is adjacent the first one of the holes 47, one or both of the internal surfaces 37a and 37b elastically deforms from a neutral position to a deformed position with respect to the other of the internal surfaces 37a and 37b that is expanded along the lateral direction with respect to the neutral position, so that the width W1 is substantially equal to the maximum cross-sectional dimension D of the shaft 56 along the lateral direction. As the shaft 56 travels into the second one of the holes 47, the expanded one or both of the internal surfaces 37a and 37b returns to the neutral position, whereby the first width W1 is less than the maximum cross-sectional dimension D of the shaft 56. Without being bound by theory, it is believed that in certain embodiments when the shaft 56 is threaded, the threads 56a (see FIG. 3) can cut into the internal surfaces 37a and 37b, for instance at the intersection 48, and thereby create deformation, for instance in the form of a track, in the internal surfaces 37a and 37b as the shaft 56 travels from the first one of the pockets 45 into the second one of the pockets 45. However, once the shaft 56 is in the second one of the pockets 45, the threads 56a do not naturally align with the track that was previously created in the internal surfaces 37a and 37b. As a result, the threads 56a would create a new track in the internal surfaces 37a and 37b in order for the shaft 56 to return to the first one of the pockets 45 in accordance with one embodiment. Because the creation of a new track would be associated with a large amount of force along a direction from the second one of the pockets 45 toward the first one of the pockets 45, interference between the threads 56a and the internal surfaces 37a and 37b assists in retention of the shaft in the second one of the pockets 45. As the shaft 56 further travels along the intersections 48 from the second one of the holes 47 into a third one of the holes 47 that is adjacent the second one of the holes 47, one or both of the internal surfaces 37a and 37b elastically deforms from a neutral position to a deformed position with respect to the other of the internal surfaces 37a and 37b that is expanded along the lateral direction with respect to the neutral position, so that the width W1 is substantially equal to the maximum cross-sectional dimension D of the shaft 56 along the lateral direction. As the shaft 56 travels into the third one of the holes 47, the expanded one or both of the internal surfaces 37a and 37b returns to the neutral position, whereby the first width W1 is less than the maximum cross-sectional dimension D of the shaft 56.

Figure 8E:
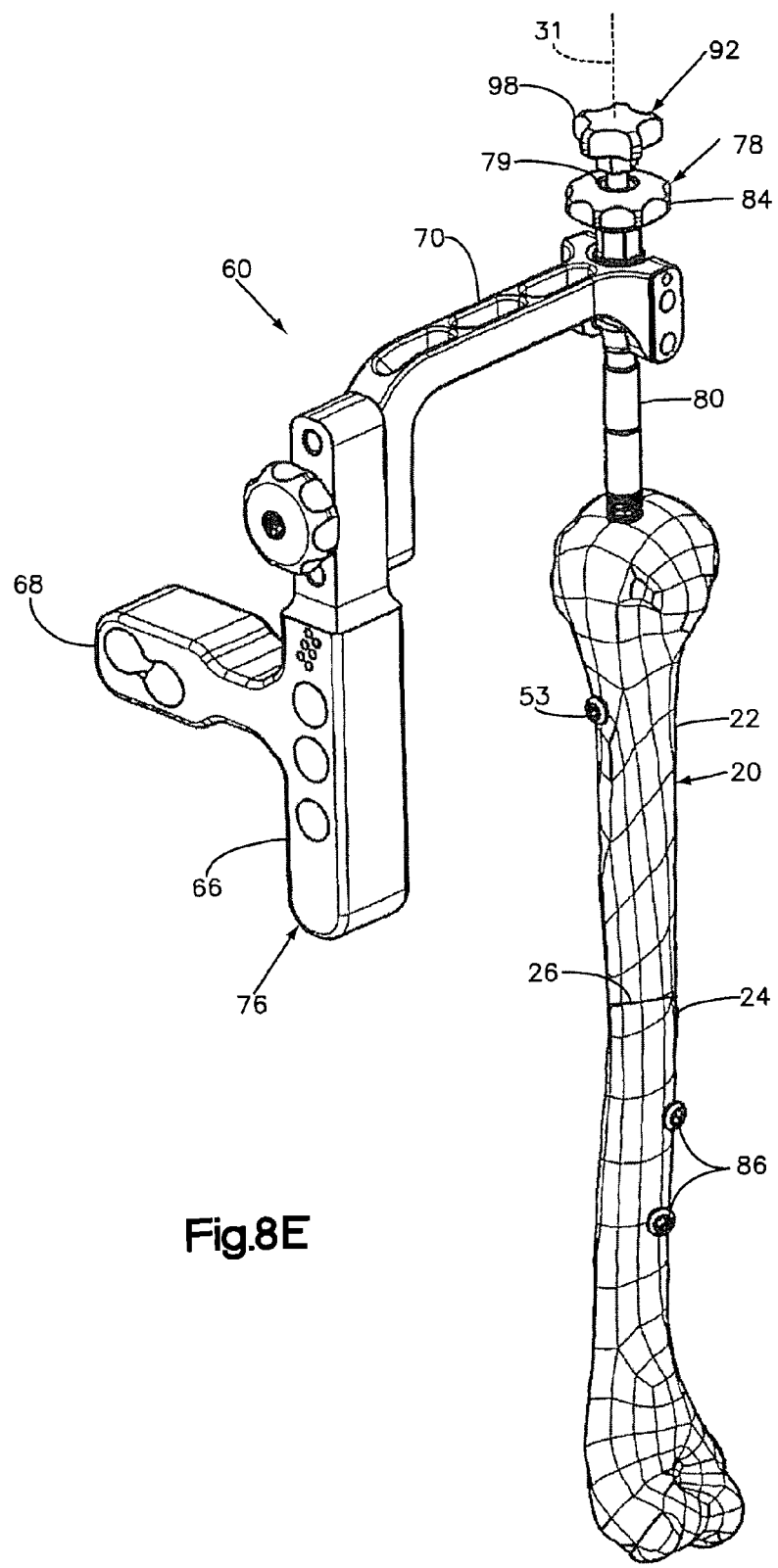
FIG. 8E is a perspective view of the fixation system illustrated in FIG. 8D.
Figure 8F:
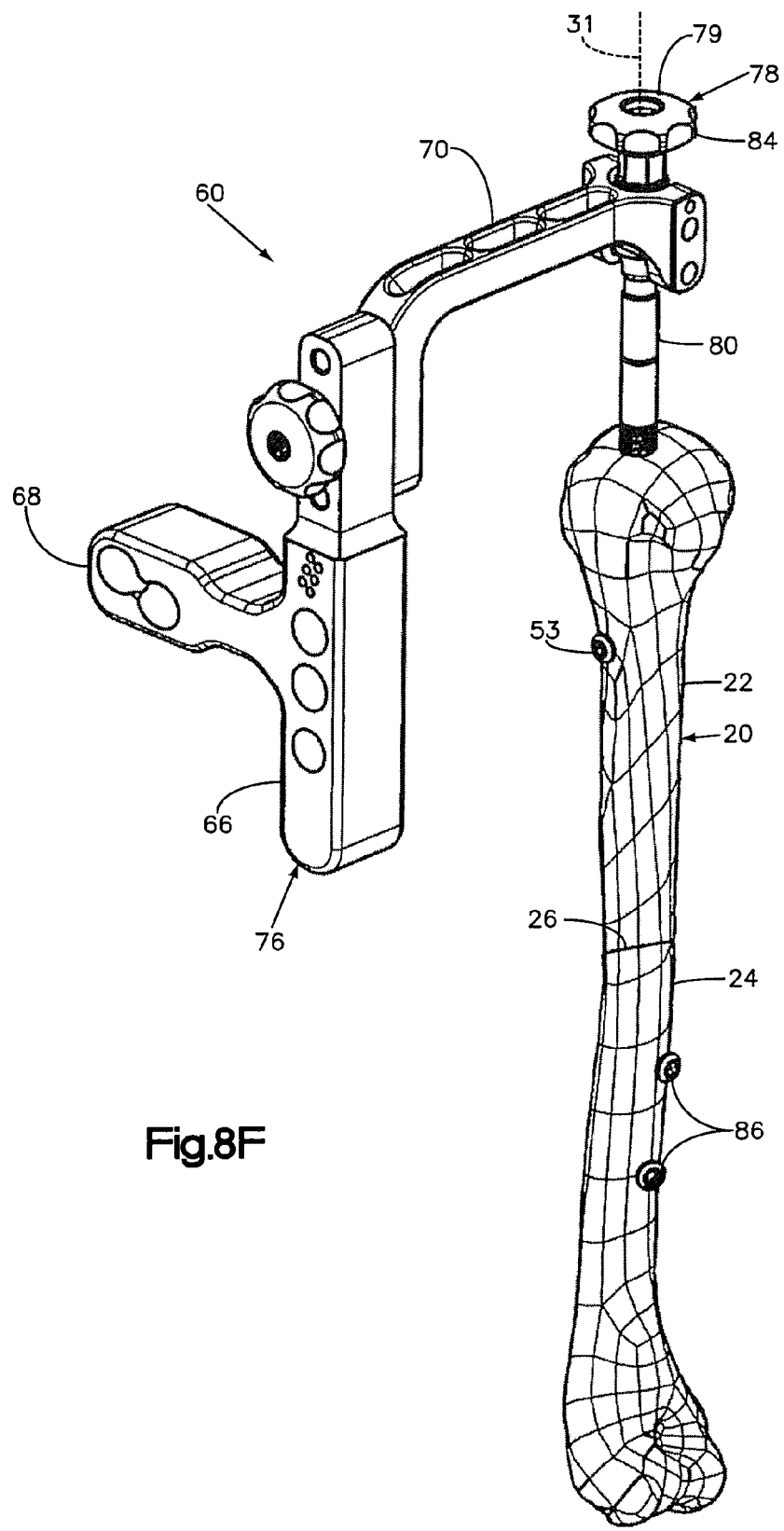
FIG. 8F is a perspective view of the fixation system illustrated in FIG. 8E, but showing the compression actuator removed such that the bone gap remains approximated.

Thus, referring to FIGS. 8D-E, once the cross-sectional distance of the shaft 56 is substantially equal to the width W1 of the intersection 48, the approximation force applied to the compression member 53 by the compression actuator 92 causes the compression member 53 to translate from a first pocket 45, past the adjacent distal intersection 48, and into a second pocket 45 that is adjacent the first pocket and spaced from the first pocket along a direction from the first portion 33 of the nail body 32 toward the second portion 35 of the nail body 32. Because the compression member 53, and in particular the shaft 56, is further fixed to the bone segment that corresponds to the first portion 33 of the nail body 32 with respect to relative longitudinal movement, movement of the compression member 53 causes the respective bone segment to translate toward the opposed bone segment. In accordance with the illustrated embodiment, the compression member 53 is fixed to the proximal bone segment 22 with respect to relative longitudinal movement, and distal movement of the compression member 53 thereby causes the proximal bone segment 22 translate distally toward the opposed distal bone segment 24, thereby approximating the bone gap 26 to a second longitudinal gap distance that is less than the gap distance D1. Continued translation of the compression member 53 within the compression slot 39 can cause the compression member 53 to translate into sequentially distal pockets 45, thereby resulting in a further reduction in the gap distance. The compression member 53 can be translated to a final one of the pockets 45, for instance, until the first and second bone segments 22 and 24 abut each other and the bone gap 26 has been reduced to a desired longitudinal distance less than the bone gap distance D1. Once the bone gap 26 has been reduced, interference between one of the intersections 48 that is disposed immediately proximal with respect to the compression member 53 provides a reactive resistive force to the compression member 53 against forces that could tend to bias the proximal and distal bone segments 22 and 24 away from each other along the longitudinal direction L, which could increase the bone gap 26.

In accordance with an alternative embodiment, as described above, the first portion 33 of the nail body can define the distal portion 36 of the nail body, such that the compression slot 39 can be defined by, and thus disposed in, the distal portion 36 of the nail body 32. Accordingly, the compression member 53 can initially be driven into the distal bone segment 24 and into a select pocket 45, such that the compression slot 39 defines at least one other pocket 45 that is disposed proximal of the select pocket (e.g., along a direction from the first portion 33 of the nail body 32 toward the second portion 35 of the nail body 32) and spaced from the select pocket any longitudinal distance as desired, such as a distance at least substantially equal to the bone gap distance D1. The brace member 78 can be thus be secured to the proximal 34 of the nail body 32 with respect to relative proximal movement along the longitudinal direction L as described above, and the compression actuator 92 can be attached to the brace member 78 and configured to bias the compression member 53 proximally along the compression slot 39, thereby translating the distal bone segment 24 proximally toward to the proximal bone segment 22 so as to approximate the bone gap 26.

It should be appreciated that the brace member 78, when connected to the intramedullary nail 30, can stabilize the intramedullary nail 30 against movement due to the biasing force F of the compression actuator 92 acting on the intramedullary nail 30 via the compression member 53. While the brace member 78 is attached to the same end of the intramedullary nail 30 that receives the compression actuator 92 in accordance with the illustrated embodiment, the brace member 78 can be attached to the intramedullary nail 30 at any location along the nail body 32, and can alternatively be attached to the bone segment that is fixed to the intramedullary nail 30 with respect to relative longitudinal movement (the distal bone segment 24 in accordance with the illustrated embodiment), such that the brace member 78, via the bone anchors 86 and the bone segment 24, stabilizes the intramedullary nail 30 against movement in response to the biasing force applied by the compression actuator 92.

Alternatively still, the implantation assembly 62 can be devoid of the brace member 78, such that the human anatomy resists the biasing force applied by the compression actuator 92. For instance, in accordance with one illustrated embodiment, the anatomical joint proximate to the distal bone segment 24 and adjacent anatomical structure can stabilize the intramedullary nail 30 via the distal bone segment 24 that is attached to the intramedullary nail 30 by the bone anchors 86. If the implantation assembly 62 is devoid of the brace member 78, the compression actuator 92 can be movably attached to the support frame 76 in the manner described above with respect to the brace member 78 or any suitable alternative manner.

It should be appreciated that because certain ones of the first plurality of bone anchor holes 40a of the first portion 33 of the nail body 32 can be disposed longitudinally outward with respect to the compression slot 39 and aligned with the compression member 53 when the compression member 53 is inserted into the compression slot 39, the shaft 93 of the compression actuator 92 can interfere with certain ones of the bone anchors 86 that might be driven through the first plurality of bone anchor holes 40 before the compression actuator 92 is disengaged from the compression member 53 and removed from the intramedullary nail 30. Thus, the compression actuator 92 and the brace member 78 can Alternatively or additionally, one or more of the first bone anchor holes 40a can be disposed at a location longitudinally inward of the compression slot 39 if desired. Alternatively still, one or more of the first bone anchor holes 40a can be offset with respect to the compression member 53 along a direction substantially perpendicular to the longitudinal direction L, such that the shaft 93 is removed from interference with bone anchors 86 that are driven through the first bone anchor holes 40a.

It should be further appreciated that while the compression actuator 92 applies the biasing force F directly to the compression member 53 in accordance with the illustrated embodiment, the abutment surface 97 of the compression actuator 92 can alternatively apply the biasing force F to the compression member 53 indirectly, for instance by applying the biasing force F to the bone segment that is aligned with the first portion 33 of the nail body (e.g., the proximal bone segment 22 in accordance with the illustrated embodiment). The distal force applied to the proximal bone segment 22 can be communicated to the compression member 53, which biases the compression member 53 to translate along the compression slot 39 in the manner described above so as to approximate the bone gap 26.

Referring now to FIG. 8E, once the bone gap 26 has been reduced, for instance such that the bone segments 22 and 24 abut each other, the compression actuator 92 can be removed. In accordance with the illustrated embodiment, the compression actuator 92 can be rotated in a disengagement direction that is opposite the engagement direction, which causes the abutment surface 97 at the distal end of the shaft 93 to translate proximally along the longitudinal direction L and retract away from the compression member 53. Continued rotation of the compression actuator 92 in the disengagement direction causes the compression actuator 92 to detach from the brace member 78, and thus the support frame 76 and the intramedullary nail 30. Once the compression actuator 92 has been detached, the intersection 48 adjacent the compression member 53 interferes with the compression member 53 and prevents the compression member 53 from translating proximally out of the final one of the pockets 45, thereby preventing anatomical distractive forces from increasing the bone gap 26. Accordingly, the compression slot 39 retains the compression member 53 in the final one of the pockets 45, thereby maintaining the first and second bone segments 22 and 24 in an abutting relationship.

Figure 9A:
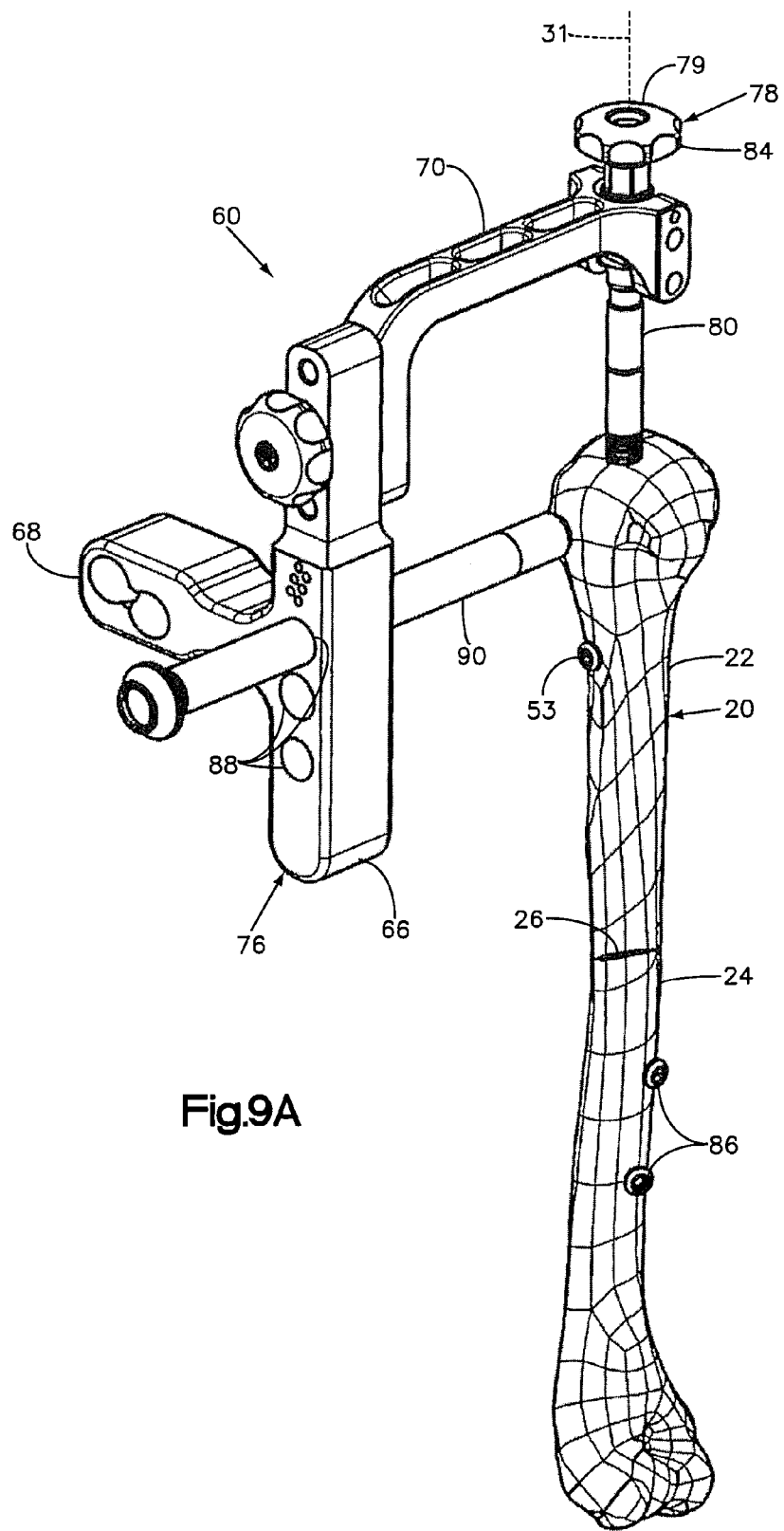
FIG. 9A is a perspective view of the fixation system illustrated in FIG. 8E, showing the aiming sleeve aligned with one of the proximal bone anchor holes.
Figure 9B:
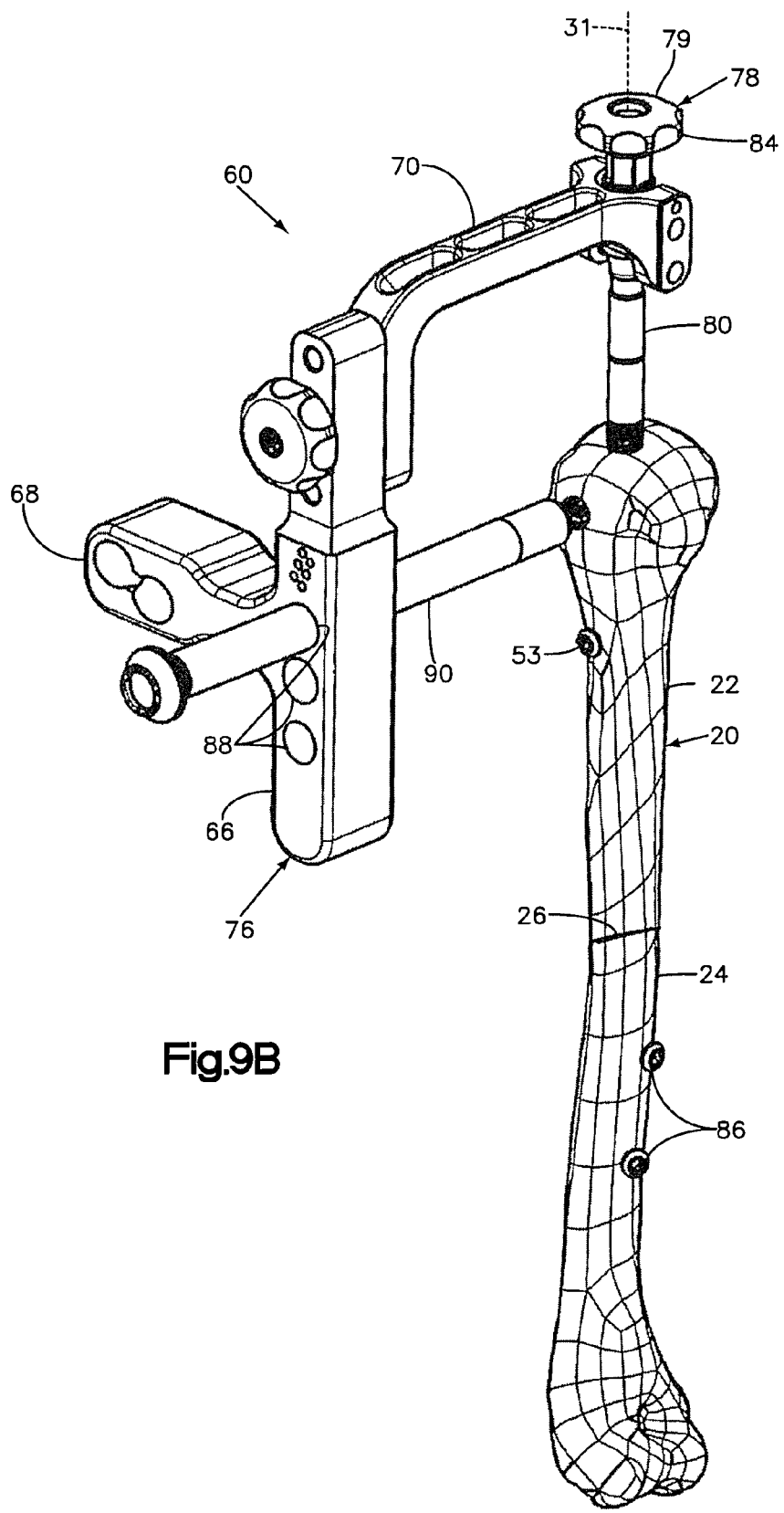
FIG. 9B is a perspective view of the fixation system illustrated in FIG. 9A, but showing a bone screw inserted into the proximal bone segment and one of the proximal bone anchor holes.
Figure 9C:
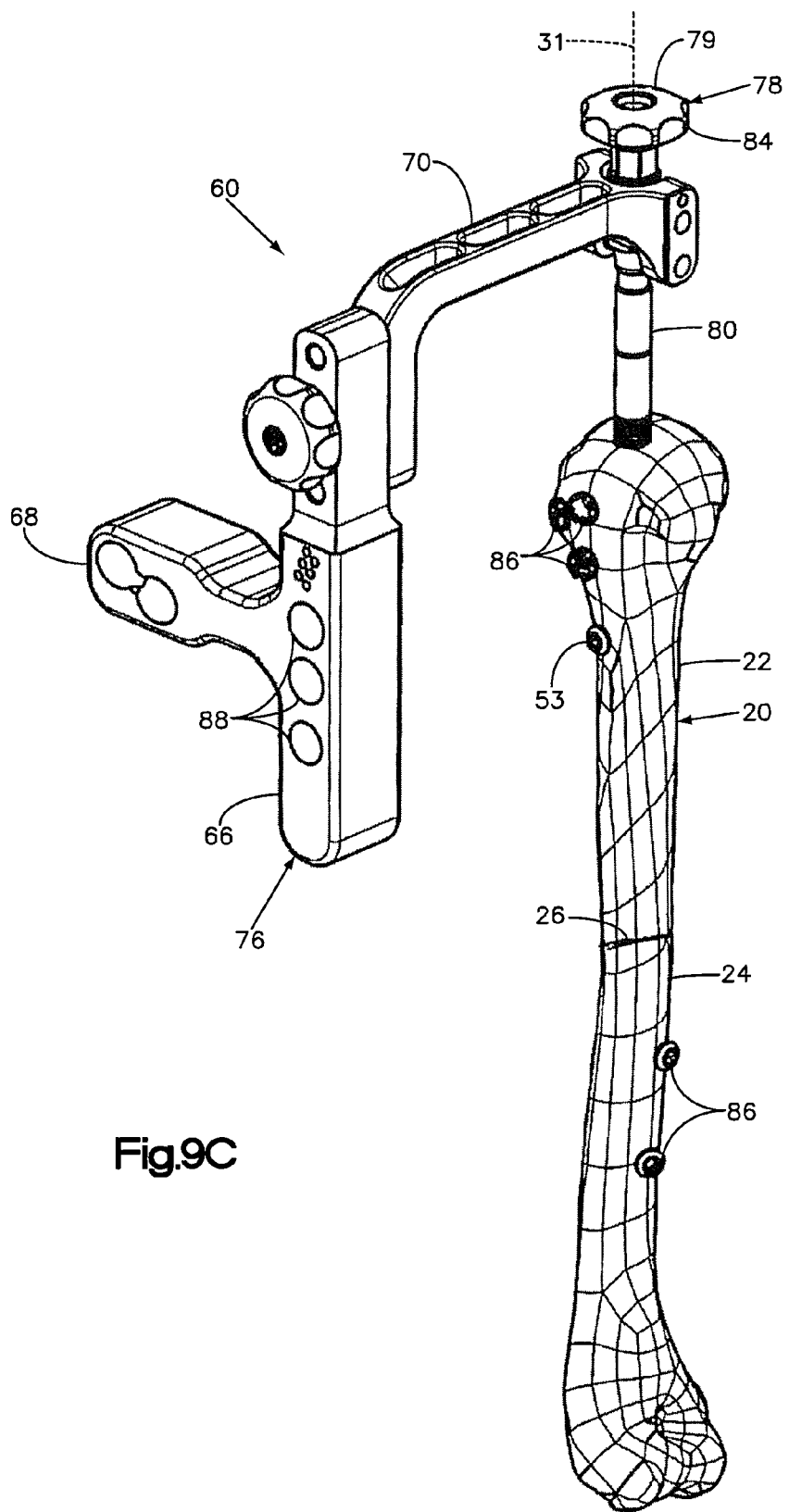
FIG. 9C is a perspective view of the fixation system illustrated in FIG. 9B, but showing a second bone screw inserted into the proximal bone segment and one of the proximal bone anchor holes.
Figure 10:
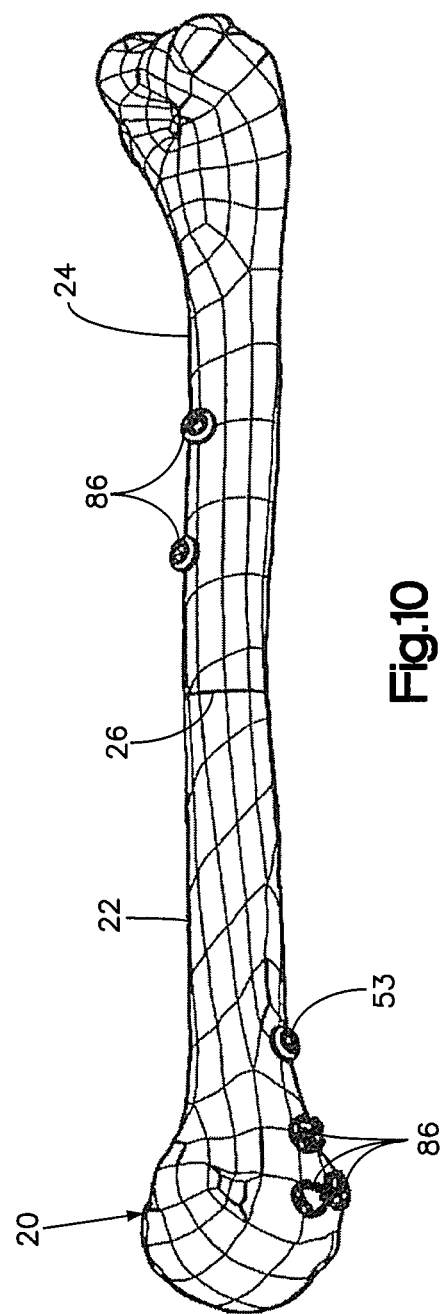
FIG. 10 is a perspective view of the fractured bone illustrated in FIG. 1, but approximated and fixed to the intramedullary nail illustrated in FIGS. 2A and 2B after the implantation assembly illustrated in FIG. 9C has been removed from the intramedullary nail.

Referring now to FIGS. 9A-C, once the compression actuator 92 has been removed from the intramedullary nail 30, the shaft 93 is also removed from interference with respect to the first bone anchor holes 40a that are disposed longitudinally outward, or proximal, with respect to of the compression slot 39. Accordingly, a plurality of bone anchors 86 can be driven into the proximal bone segment 22 that corresponds to the first portion 33 of the nail body 32 and into the corresponding first bone anchor holes 40a that extend into or through the first portion 33 of the nail body 32. Because bone anchors 86 had previously fastened the distal bone segment 24 to the second portion 35 of the nail body 32 as illustrated in FIG. 6, attachment of the proximal bone segment 22 to the first portion 33 of the intramedullary nail 30 secures the intramedullary nail 30 to the proximal and distal bone segments 22 and 24 separated by the previously-approximated bone gap 26. For instance, as illustrated in FIG. 9A, an aiming sleeve 90 can be inserted through one of a plurality of guide apertures 88 that extend through the frame member 87 so as to align the aiming sleeve 90 with one of the first plurality of bone anchor holes 40 that extend into or through the first portion 33 of the nail body 32. Accordingly, a bone anchor 86 can be inserted into a cannulation of the aiming sleeve 90 and driven into the proximal bone segment 22 and subsequently into or through bone anchor hole 40 so as to fix the first portion 33 of the nail body 32 to the bone segment 22. As many bone anchors 86 can be attached to the bone segment 22 and the intramedullary nail 30 as desired until the intramedullary nail 30 is suitably fastened to the first or proximal bone segment 22. The support frame 76 and the brace member 78 can then be removed from the intramedullary nail 30 as illustrated in FIG. 10. The compression member 53 can remain implanted in the long bone 20 and the compression slot 39 as illustrated in FIG. 10, or can be removed from the compression slot 39 prior to completing the surgical procedure.

In accordance with one embodiment, and referring to FIGS. 1-10 in general, a method 33 can be provided for reducing the bone gap 26 of the long bone 20, the bone gap 26 separating the first bone segment 22 from the second bone segment 24 hat is spaced from the first bone segment 22 along the longitudinal direction L. The method includes the step of inserting the intramedullary nail 30 into the medullary canal 23 of the long bone 20 such that a portion, such as the intermediate portion 38, of the intramedullary nail 30 extends across the bone gap 26. The method can further include the step of fixing the intramedullary nail 30 to one of the first and second bone segments 22 and 24, respectively, with respect to longitudinal movement relative to the fixed one of the first and second bone segments 22 and 24, respectively. The method can further include the step of inserting the compression member 53 at least into the other of the first and second bone segments 22 and 24 and further at least into a first pocket 45 of the scalloped compression slot 39 that is defined by the intramedullary nail 30. The method can further include the step of applying a distal approximation force to the compression member 53 while bracing the intramedullary nail 30 so as to cause the compression member 53 to travel from the first pocket 45, across a necked portion, which can be defined by one of the intersections 48 as described above, the necked portion having a cross sectional dimension less than a corresponding cross-sectional dimension of the compression member 53, for instance along the lateral direction A, and into a second pocket 45 that is spaced from the first pocket 45 along the longitudinal direction L so as to reduce the bone gap 26. The method can include any additional steps as described herein.

Figure 11C:
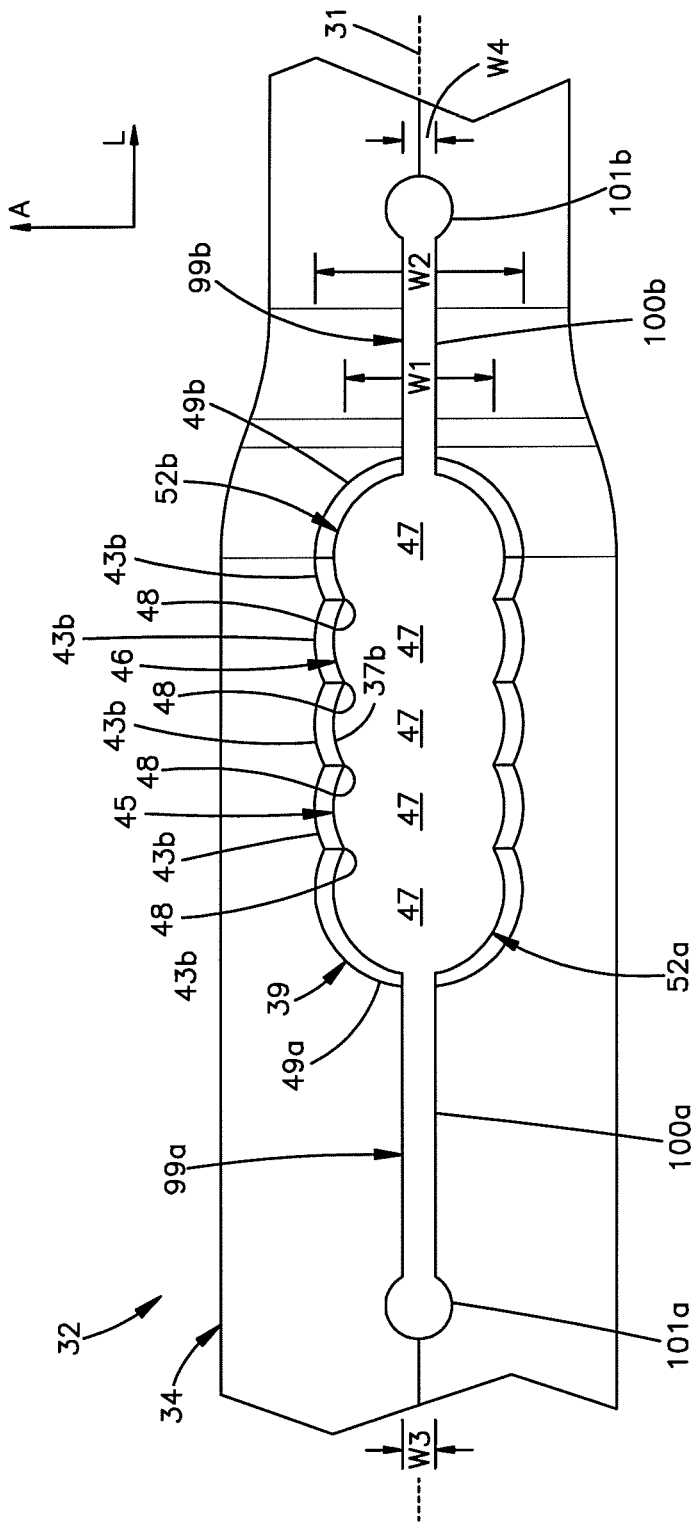
FIG. 11C is an enlarged side elevation view of a portion of the intramedullary nail illustrated in FIG. 11A.

It should be appreciated that that the intramedullary nail 30 can be constructed in accordance with any suitable alternative embodiment as desired. For instance, referring to FIGS. 11A-C, the intramedullary nail 30 includes least one relief slot that extends out from the compression slot 39 and terminates in the nail body 32. In accordance with the illustrated embodiment, the intramedullary nail 30 can include at least one relief slot, such as a first or proximal relief slot 99a and a second or distal relief slot 99b that extend into or through the nail body 32 along the transverse direction T. The first relief slot 99a is open to the compression slot 39, and is open to the outermost pocket 52a in accordance with the illustrated embodiment. The second relief slot 99b is open to the compression slot 39, and is open to the innermost pocket 52b in accordance with the illustrated embodiment. The first relief slot 99a can define a main portion 100a that extends proximally from the compression slot 39, and a terminates at a terminal end 101a that extends proximally from the main portion 100a and is proximally spaced with respect to the compression slot 39, and distally spaced from at least one or more up to all of the first holes 40a. The second relief slot 99b can define a main portion 100b that extends distally from the compression slot 39, and terminates at a terminal end 101b that is distally spaced with respect to the compression slot 39.

The first and second relief slots 99a and 99b define respective widths W3 and W4 along the lateral direction A, and thus substantially parallel to the first and second widths W1 and W2, respectively, for instance at their respective main portions 100a and 100b. The widths W3 and W4 can be substantially equal to each other or different. For instance, the width W3 of the main portion 100a can be greater or less than the width W4 of the main portion 100b. Furthermore, the widths W3 and W4 can be substantially constant along the length of the first and second main portions 100a and 100b, respectively. Alternatively, the width W3 can increase or decrease along the proximal direction away from the compression slot 39. Similarly, the width W4 can alternatively increase or decrease along the distal direction away from the compression slot 39. The respective terminal ends 101a and 101b can define cylindrical holes that overlap the proximal and distal ends, respectively, of the main portions 100a and 100b, and can alternatively define any suitable shape.

The first and second relief slots 99a and 99b can reduce the rigidity of the nail body 32 immediately adjacent the outermost and innermost pockets 52a and 52b along the longitudinal direction L. For instance, the first and second relief slots 99a and 99b can define respective hinges at the corresponding terminal ends 101a and 101b. In response to an applied force to the compression member 53 that biases the internal surfaces 37a and 37b away from each other, the hinges defined by the first and second relief slots 99a and 99b can expand along the lateral direction A, thereby increasing the third and fourth widths W3 and W4, which in turn reduces the force required to be applied to the compression member 53 so as to overcome the retention force and expand one or both of the first and second internal surfaces 37a and 37b with respect to the other of the first and second internal surfaces 37a and 37b a distance that increases the first width W1 to a distance substantially equal to the maximum cross-sectional dimension D (see FIG. 3) of the compression member shaft 56, as compared to the force required to be applied to the compression member 53 so as to expand one or both of the first and second internal surfaces 37a and 37b with respect to the other of the first and second internal surfaces 37a and 37b a distance that increases the first width W1 to a distance substantially equal to the maximum cross-sectional dimension D (see FIG. 3) of the compression member shaft 56 when the intramedullary nail 30 does not include the first and second relief slots 99a and 99b. It should be appreciated that the first and second internal surfaces 37a and 37b can reduce both the approximation force and the retention force, and can also reduce debris that might be created due to translation of the shaft 56 along the first and second internal surfaces 37a and 37b. The first and second relief slots 99a and 99b can be dimensioned, for instance at the third and fourth widths W3 and W4, so as to determine a predictable approximation force, while providing a sufficiently high retention force with a minimal amount of debris during operation.

Although the disclosure has been described in detail, it should be understood that various changes, substitutions, and alterations can be made herein without departing from the spirit and scope of the invention as defined by the appended claims. Moreover, the scope of the present disclosure is not intended to be limited to the particular embodiments described in the specification. Furthermore, structure, features, and methods described in combination with one embodiment as described herein can be applicable to any other embodiment described herein absent a statement to the contrary. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present disclosure.

We claim:

1. A bone fixation assembly comprising:
   an intramedullary nail having an elongate nail shaft and defining a compression slot that is elongate along a substantially distal direction;
   a compression member sized to be received in the compression slot and translated in the distal direction from a first position in the compression slot to a second position in the compression slot, wherein the compression slot is configured to retain the compression member in the second position after being translated from the first position to the second position; and
   an implantation assembly configured to apply a force to the compression member to translate the compression member from the first position to the second position, the implantation assembly including:
   a support frame;
   a brace member having an elongate shaft defining a proximal end that is configured to be supported by the support frame, and a distal end that spaced from the proximal end substantially in a distal direction and is configured to attach to the intramedullary nail so as to secure the intramedullary nail with respect to movement in the distal direction relative to the support frame, wherein the elongate shaft defines a cannulation extending from the proximal end to the distal end; and
   a compression actuator having an elongate actuator shaft defining a proximal actuator end and a distal actuator end spaced from the proximal actuator end substantially in the distal direction, the elongate actuator shaft sized to be received within the cannulation of the brace member, wherein the compression actuator is movable within the cannulation of the brace member in the distal direction such that a portion of the compression actuator extends out from the brace member in the distal direction; wherein the elongate nail shaft defines a proximal nail end and a distal nail end spaced substantially in the distal direction from the proximal nail end, the compression slot extends into a first portion of the nail shaft, and the elongate nail shaft further defines a nail cannulation extending from the proximal nail end into the compression slot; and the compression slot is scalloped so as to define at least a first pocket and a second pocket spaced from the first pocket along the distal direction.

2. A method of reducing a bone gap of a long bone, the bone gap separating a first bone segment from a second bone segment that is spaced from the first bone segment along a longitudinal direction, the method comprising:
   coupling a brace member to a support frame, the brace member having an elongate shaft defining a proximal end and a distal end spaced from the proximal end substantially in a distal direction, the elongate shaft defining a cannulation that extends from the proximal end to the distal end;
   coupling an intramedullary nail to the distal end of the brace member such that the intramedullary nail extends substantially in the distal direction from the brace member;
   implanting the intramedullary nail into a medullary canal of the long bone such that a portion of the intramedullary nail extends across the bone gap;
   fixing the intramedullary nail to the second bone segment; and
   inserting a compression member configured as a bone screw into the first bone segment, such that the compression member extends at least into a compression slot of the intramedullary nail and terminates between the intramedullary nail and the support frame; and;
   translating a compression actuator within the cannulation of the brace member in the distal direction, such that the compression actuator applies a force to the compression member, thereby causing the compression member to translate in the distal direction in the compression slot, thereby reducing the bone gap;
   wherein the compression slot is scalloped so as to define at least a first pocket and a second pocket spaced from the first pocket along the distal direction and the compression actuator is translated so as to cause the compression member to move from the first pocket to the second pocket.

3. A method of reducing a bone gap of a long bone, the bone gap separating a first bone segment from a second bone segment that is spaced from the first bone segment along a longitudinal direction, the method comprising:
   inserting an intramedullary nail into a medullary canal of the long bone such that a portion of the intramedullary nail extends across the bone gap;
   fixing the intramedullary nail to one of the first and second bone segments with respect to movement in the longitudinal direction relative to the fixed one of the first and second bone segments;
   inserting a compression member at least into the other of the first and second bone segments and at least into a slot of the intramedullary nail, the slot elongate along the longitudinal direction;
   applying a force to the compression member along the longitudinal direction so as to cause the compression member to travel within the slot along the longitudinal direction from a first position to a second position, thereby causing the other of the first and second bone segments to move toward the fixed one of the first and second bone segments to reduce the bone gap; and
   providing resistance via the slot against movement of the compression member from the second position back to the first position;
   wherein the compression slot defines a plurality of holes that overlap each other along the longitudinal direction, and the step of applying the force to the compression member causes the compression member to translate along the longitudinal direction from a first of the plurality of holes to a second of the plurality of holes.

* * * * *